US009205270B2

(12) United States Patent
Pathak et al.

(10) Patent No.: US 9,205,270 B2
(45) Date of Patent: Dec. 8, 2015

(54) METHOD AND APPARATUS FOR THE DIAGNOSIS AND PROGNOSIS OF ACTIVE IMPLANTS IN OR ATTACHED TO BIOLOGICAL HOSTS OR SYSTEMS

(75) Inventors: Bogdan Amaru Pathak, Milan, MI (US); Walter J. Keller, III, Bridgeville, PA (US)

(73) Assignee: NOKOMIS, INC, Charleroi, PA (US)

( * ) Notice: Subject to any disclaimer, the term of this patent is extended or adjusted under 35 U.S.C. 154(b) by 1216 days.

(21) Appl. No.: 13/106,412

(22) Filed: May 12, 2011

(65) Prior Publication Data
US 2011/0320170 A1  Dec. 29, 2011

Related U.S. Application Data

(60) Provisional application No. 61/398,513, filed on Jun. 28, 2010.

(51) Int. Cl.
*G01N 33/48* (2006.01)
*A61N 1/372* (2006.01)

(52) U.S. Cl.
CPC ........ *A61N 1/37229* (2013.01); *A61N 1/37223* (2013.01); *A61N 1/37282* (2013.01); *A61N 2001/37294* (2013.01)

(58) Field of Classification Search
USPC .......................................................... 702/19
See application file for complete search history.

(56) References Cited

U.S. PATENT DOCUMENTS

| | | | |
|---|---|---|---|
| 5,218,294 A | 6/1993 | Soiferman | |
| 5,227,800 A | 7/1993 | Huguenin et al. | |
| 5,302,830 A | 4/1994 | Shivanandan | |
| 5,424,633 A | 6/1995 | Soiferman | |
| 5,517,110 A | 5/1996 | Soiferman | |
| 5,668,342 A | 9/1997 | Discher | |
| 5,714,888 A | 2/1998 | Naujoks | |
| 6,049,301 A | 4/2000 | Weagant | |
| 6,057,765 A | 5/2000 | Jones et al. | |
| 6,163,259 A | 12/2000 | Barsumian et al. | |
| 6,496,703 B1 | 12/2002 | da Silva | |
| 6,720,905 B2 | 4/2004 | Levitan et al. | |
| 6,759,863 B2 | 7/2004 | Moore | |
| 6,765,527 B2 | 7/2004 | Jablonski et al. | |

(Continued)

OTHER PUBLICATIONS

Notification Concerning Transmittal of International Preliminary Report on Patentability; International Bureau.

*Primary Examiner* — Sujoy Kundu
*Assistant Examiner* — Steven J Malone
(74) *Attorney, Agent, or Firm* — James Ray and Assoc., LLC

(57) ABSTRACT

A method and apparatus to measure and analyze electromagnetic emissions from implanted electronics to accomplish at least one of: detect and identify an active implant comprising electronics implanted in a biological host, diagnose the health of individual electronics as well as their health as an ensemble, and predict probable degradation of individual electronics, degradation of the electronic ensemble, and of the active implant in an automated fashion. The methods comprise filtering techniques to extract the information about the active implant's electronics by filtering out relevant biological effects induced by the active implant's biological situation. Said detection, identification, diagnosis, and prognosis are based on the measurement of intentional and unintentional electromagnetic emissions that emanate from the implant electronics of the active implant in a given biological situation.

130 Claims, 9 Drawing Sheets

(56) References Cited

U.S. PATENT DOCUMENTS

| | | |
|---|---|---|
| 6,825,456 B2 | 11/2004 | Chadwick et al. |
| 6,897,777 B2 | 5/2005 | Holmes et al. |
| 6,927,579 B2 | 8/2005 | Blades |
| 6,985,771 B2 | 1/2006 | Fischell et al. |
| 7,130,624 B1 | 10/2006 | Jackson et al. |
| 7,138,936 B2 | 11/2006 | Duff et al. |
| 7,188,037 B2 | 3/2007 | Hidehira |
| 7,391,356 B2 | 6/2008 | Brumley et al. |
| 7,512,511 B1 | 3/2009 | Schultz et al. |
| 7,515,094 B2 | 4/2009 | Keller, III |
| 7,609,199 B2 | 10/2009 | Nishijima et al. |
| 7,639,178 B1 | 12/2009 | Mulbrook et al. |
| 7,777,671 B2 | 8/2010 | Schnitzer et al. |
| 7,777,672 B2 | 8/2010 | Schnitzer et al. |
| 7,844,341 B2 * | 11/2010 | Von Arx et al. ......... 607/60 |
| 8,063,813 B1 | 11/2011 | Keller |
| 8,131,564 B2 * | 3/2012 | Dicks et al. ............ 705/2 |
| 2005/0165456 A1 * | 7/2005 | Mann et al. ............ 607/30 |
| 2006/0259082 A1 * | 11/2006 | Youker et al. .......... 607/7 |
| 2007/0279071 A1 | 12/2007 | Orton |
| 2008/0103555 A1 | 5/2008 | Dicks et al. |
| 2009/0030487 A1 * | 1/2009 | Lang ..................... 607/60 |
| 2010/0114216 A1 * | 5/2010 | Krause et al. .......... 607/5 |
| 2010/0123453 A1 | 5/2010 | Pauly et al. |
| 2010/0125438 A1 | 5/2010 | Audet |
| 2011/0270337 A1 * | 11/2011 | Doerr et al. ............ 607/6 |
| 2012/0179812 A1 | 7/2012 | Keller, III |
| 2012/0223403 A1 | 9/2012 | Keller, III et al. |
| 2012/0226463 A1 | 9/2012 | Keller et al. |

* cited by examiner

Legend
1 - Biological Situation
2 - Implanted Electronics
5 - Active Implant
6 - Loop Antenna
9 - Conformal Antennas
10 - Signal Processor
14 - Receiving Antenna(s)
15 - Dipole Antenna

METHOD AND APPARATUS FOR THE DIAGNOSIS AND PROGNOSIS OF ACTIVE IMPLANTS IN OR ATTACHED TO BIOLOGICAL HOSTS OR SYSTEMS

CROSS-REFERENCE TO RELATED APPLICATIONS

This patent application is related to and claims priority from U.S. Provisional Patent Application Ser. No. 61/398,513 filed Jun. 28, 2010 and is herein incorporated by reference.

FIELD OF THE INVENTION

The present invention is in the technical field of monitoring, diagnosis, and prognosis of electrically enabled devices. More particularly, the present invention is in the technical field of monitoring, diagnosis, and prognosis of electrically enabled devices implanted in or attached to biological hosts or systems using the unintended electromagnetic emissions of said electrically enabled devices.

BACKGROUND OF THE INVENTION

The nuances of monitoring, diagnosing, and predicting electronic device functionality, degradation, and failure are numerous and complex. This complexity is compounded by device interaction with biological hosts. The literature is full of different electrical models of biological tissues described for specific applications involving electromagnetic fields. Examples include references for computed tomography (CT) scans, radio-frequency identification (RFID) tags, specific absorbed radiation (SAR) testing, etc. These various references cite biological tissues' ability to attenuate and distort electromagnetic radiation, but none provide a way to effectively reconstruct an original signal. Signal distortion is particularly evident in electronically enabled medical implants and animal tracking implants, where great pains are taken to place the device transceiving antennas or coils close to the interface between the biological host and free space. Therefore, it has been found necessary to provide an apparatus that utilizes deterministic, statistical, and stochastic methods to effectively eliminate the biological interference so as to simplify the process of monitoring, diagnosing, and predicting electronically enabled device functionality, degradation, and failure utilizing intended and unintended emissions.

SUMMARY OF THE INVENTION

Many of the fundamental concepts of the present invention are outlined in U.S. Pat. No. 7,515,094 and U.S. patent application Ser. No. 12/551,635 and are herein incorporated by reference.

The present invention provides a method and apparatus for 1) detecting, identifying, and/or locating electrically enabled devices implanted in or attached to biological hosts or systems; 2) discriminating between and diagnosing various states of functionality, degradation, and failure of electrically enabled devices implanted in or attached to biological hosts or systems; and 3) predicting or generating a prognosis for the course and timeframe of function, degradation, or failure of electrically enabled devices implanted in or attached to biological hosts or systems. Many of the preferred methods and apparatus utilize at least one of the unintended and intended electromagnetic emissions of electrically enabled or powered systems.

This patent addresses the issues of monitoring, validating, diagnosing, and predicting either proper device functionality or device degradation and failure throughout the device's functional lifetime. This includes during manufacturing, transport, implantation, function within a host, degradation, end-of-life explantation, and post-life testing.

More specifically, this invention comprises a robust method and apparatus that measures subtle intended and unintended electromagnetic (EM) signatures radiated by electrically enabled devices implanted in or attached to biological hosts or systems to accomplish items 1, 2, and 3 as listed previously. This especially targets, but is not limited to, those electrically enabled devices implanted in or attached to biological hosts or systems used in clinical medicine. This apparatus is able to detect, identify, diagnose, and predict the state of implant electronics and the tissues or materials that affect them noninvasively, wirelessly or without breaking a tissue layer, through plant and animal tissue, or any other form of biological cells as well as observe a myriad of electronic components in both states of good health and disrepair. Changes to the signatures have been observed that allow the system to accomplish items 1, 2, and 3 as listed previously, including the ability to predict when said electrically enabled device will fail, or when it has sustained sufficient damage, degradation or aging to alter its nominal behavior. The predictions can even be made when the changes in the device's behavior are unnoticeable, or hardly noticeable, to the device user, or cannot be articulated because of biological tissue preventing access to the device.

In one embodiment the invention is an emissions measurement device used to collect at least one of unintentional and intentional emissions emitted by at least one electronic device implanted in a biological host comprising, at least one antenna, a receiver, a data processing means, and a data storage means, wherein said emissions measurement device is used to collect at least one of an unintentional emission and an intentional emission emitted by at least one electronic device implanted in a biological host. In another embodiment the electronic device is attached externally to the biological host. In still another embodiment said at least one antenna is positioned on an external epidermal layer of the biological host. In another embodiment said at least one antenna is a conformal antenna adapted to conform to the external epidermal layer of the biological host. In another embodiment conformal antenna's material properties match the impedance of a tissue of the biological host to improve the collection of emissions. In another embodiment said conformal antenna's material properties match the impedance of the external epidermal layer of the biological host to improve the collection of emissions. In another embodiment said receiver comprises a self-tuning matching network connected to the at least one antenna to match the impedance of a tissue of the biological host. In another embodiment at least one antenna is a conformal antenna intended to conform to an external epidermal layer of the biological host. In another embodiment the at least one antenna is implanted in the biological host. In another embodiment the at least one antenna is positioned at a stand-off location from the biological host. In another embodiment the measurement device detects at least one electronic device within the biological host. In another embodiment the measurement device identifies at least one electronic device within the biological host. In another embodiment the measurement device performs diagnostics on the at least one electronic device. In another embodiment the measurement device performs diagnostics on the at least one electronic device, and wherein the measurement device receives a near field emission of the electronic device to enhance the amplitude of the emissions received or identifying characteristics of the received emissions. In another embodiment the at least one antenna is an antenna structure located circumcentrically around the biological host that contains the at least one electronic device. In another embodiment the biological host is moved through the antenna structure that surrounds the biological host. In another embodiment the at least one antenna moves around the biological host during measurement. In another embodiment the antenna structure is mounted to a support structure that moves around the biological host for measurement purposes. In another embodiment the biological host is located on a support structure that moves through the antenna structure for measurement purposes. In another embodiment the measurement device is configured to measure the emissions of the implanted electronics across at least one electromagnetic interface of a media with a relative permittivity greater than 1. In another embodiment the measurement device is configured to measure the emissions of the implanted electronics across at least one electromagnetic interface of a biological tissue. In another embodiment the measurement device stores implanted electronic device histories. In another embodiment the measurement device further comprises a device for storing biological host information for signature modification. In another embodiment the measurement device further comprises a device capable of measuring and diagnosing a state of an active implant using at least one of the active implant's emissions during manufacturing of said active implant. In another embodiment the measurement device further comprises a device capable of measuring and diagnosing a state of an active implant using at least one of the active implant's emissions at the implantation facility. In another embodiment the measurement device further comprises a device capable of measuring and diagnosing a state of an active implant using at least one of the active implant's emissions to verify device integrity prior to implantation. In another embodiment the measurement device further comprises a device capable of measuring and diagnosing the state of the active implant using at least one of the active implant's unintended or intended emissions immediately after implantation. In another embodiment the measurement device further comprises a device capable of measuring and diagnosing the state of the active implant using at least one of the active implant's unintended or intended emissions periodically throughout the device's lifetime. In another embodiment the measurement device further comprises a device capable of measuring and diagnosing the state of the active implant using at least one of the active implant's unintended or intended emissions during device degradation or failure. In another embodiment the measurement device further comprises a device capable of measuring and diagnosing the state of the active implant using at least one of the active implant's unintended or intended emissions after explantation. In another embodiment the measurement device further comprises a device capable of measuring and diagnosing the state of the active implant using at least one of the active implant's unintended or intended emissions during post failure testing. In another embodiment the measurement device further comprises a device capable of detecting a device whose location within the biological host changes over time. In another embodiment said measurement device is capable of detecting an electronic device that passes from the inside to the outside of the biological host. In another embodiment said measurement device is capable of interpreting electromagnetic emissions whose signatures are modified by at least one biological tissue layer. In another embodiment said measurement device is capable of determining at least one of, a state of functionality and a state of degradation of an implant after said implant has been subjected to an electrical discharge. In another embodiment said measurement device is capable of determining at least one of a state of functionality and a state of degradation of an implant's electronics after said implant's electronics have been illuminated. In another embodiment said measurement device is capable of determining the identity of an implanted electronic device by analyzing emitted electromagnetic radiation from said implanted electronics device. In another embodiment said device predicts the lifespan of any implanted electronics. In another embodiment said measurement device predicts a lifespan of said electronic device wherein said electronic device is implanted. In another embodiment said measurement device uses a measurement of at least one unintended electromagnetic emission to provide health monitoring of at least one electronic device implanted in a biological host. In another embodiment said measurement device uses a measurement of at least one unintended electromagnetic emission to provide diagnostics of at least one electronic device implanted in a biological host. In another embodiment said measurement device uses a measurement of an unintended electromagnetic emission to predict failure of said at least one electronic device implanted in a biological host. In another embodiment said measurement device uses a measurement of unintended electromagnetic emissions to track at least one of a plurality of electronics aging effects on said at least one electronic device implanted in a biological host. In another embodiment said measurement device uses a measurement of unintended electromagnetic emissions to provide non-invasive detection of said at least one electronic device implanted in a biological host. In another embodiment said measurement device uses a measurement of unintended electromagnetic emissions to provide non-invasive identification of said at least one electronic device implanted in a biological host. In another embodiment said measurement device uses a measurement of unintended electromagnetic emissions to non-invasively locate said at least one electronic device implanted in a biological host. In another embodiment wherein said measurement device uses a measurement of at least one intended electromagnetic emission to provide health monitoring of at least one electronic device implanted in a biological host. In another embodiment said measurement device uses a measurement of at least one intended electromagnetic emission to provide diagnostics of at least one electronic device implanted in a biological host. In another embodiment said measurement device uses a measurement of an intended electromagnetic emission to predict failure of said at least one electronic device implanted in a biological host. In another embodiment said measurement device uses a measurement of intended electromagnetic emissions to track at least one of a plurality of electronic aging effects of said at least one electronic device implanted in a biological host. In another embodiment said measurement device uses a measurement of intended electromagnetic emissions to provide non-invasive detection of said at least one electronic device implanted in a biological host. In another embodiment said measurement device uses a measurement of intended electromagnetic emissions to provide non-invasive identification of said at least one electronic device implanted in a biological host. In another embodiment said measurement device uses a measurement of intended electromagnetic emissions to non-invasively locate said at least one electronic device implanted in a biological host. In another embodiment said measurement device verifies that said at least one electronic device implanted in a biological host has been implanted properly. In another embodiment said measurement device is capable of detecting, identifying, and locating a non-stationary implant within the biological host. In another embodiment said measurement device is capable of determining if a non-stationary implant has been ejected from the biological host. In another embodiment said measurement device is capable of determining if said at least one electronic device is on or off at any given time. In another embodiment said measurement device determines a degree of change observed as said at least one electronic device degrades. In another embodiment said measurement device determines a degree of change observed as said at least one electronic device degrades, and ultimately fails, along with the types of changes apparent in two different, but functionally connected devices. In another embodiment said measurement device comprises a library of devices and device signatures to compare and assess the health of said at least one electronic device. In another embodiment said measurement device comprises a substantially skull shaped fixture to compensate for at least one factor present in vivo for projection to a realistic environment when at least one electronic device implanted in a biological host. In another embodiment said measurement device comprises a protocol for signature collection to assure proper collection of signature data without damaging the at least one electronic device implanted in a biological host. In another embodiment said measurement device elucidates the differences between different categories of failures. In another embodiment said measurement device provides general electronic degradation characteristics that are general to any electronic implant. In another embodiment said measurement device provides general electronic degradation characteristics that are specific to subsystems of classes of electronics implant in cases where said at least one electronic device implanted in a biological host is not fully identified. In another embodiment said measurement device provides for implant specific degradation detection via a specified signature database. In another embodiment said measurement device provides the ability to complete health monitoring on non-implanted electronics. In another embodiment said measurement device provides a methodology that uses changes in low power emissions from the electronics embedded in implants to determine the health of the device. In another embodiment an electromagnetic field is used to enhance the unintended emissions of the at least one electronic device implanted in the biological host. In another embodiment an electromagnetic field generation apparatus is used to generate an electromagnetic field that is absorbed by the at least one electronic device and subsequently re-emitted at one of a same or a different frequency as the electromagnetic field and measured by the emission measurement device. In another embodiment an electromagnetic field is generated external to the biological host and projected onto the biological host. In another embodiment an electromagnetic field is generated internal to the biological host and internally launched into the biological host.

In yet another embodiment the invention is an emissions measurement device used to collect at least one of unintentional and intentional emissions emitted by at least one electronic device implanted in a biological host comprising, at least one antenna, a receiver, a data processing means, and a data storage means, wherein said emissions measurement device is used to collect at least one of an unintentional emission and an intentional emission emitted by at least one electronic device implanted in a biological host, said emission measurement device being configured to measure the emissions of the implanted electronics across at least one electromagnetic interface of a biological tissue, wherein said measurement device determines a degree of change observed as said at least one electronic device degrades, wherein said emissions measurement determines distinct electrical states for at least one component of said at least one electronic device, wherein the distinct electrical states are selected from the group comprising a nominal electronic function, a degraded electronic function, a failed electronic function and a combination thereof.

In yet another embodiment the invention is an emission measurement device used to collect unintended signatures emitted by at least one biological implant comprising, at least one antenna, a receiver, a data processing means, and a data storage means, wherein said emissions measurement device is used to collect at least one unintended signatures emitted by at least one biological implant implanted in a biological implant recipient. In another embodiment said emissions measurement device operates in the RF frequency range to collect unintended signatures from an implant embedded into said at least one biological implant recipient. In another embodiment said emissions measurement device operates in the microwave frequency range to collect unintended signatures from an implant embedded into said at least one biological implant recipient. In another embodiment said electromagnetic measurement device operates at infrared wavelengths to collect unintended signatures from an implant embedded into said at least one biological implant recipient. In another embodiment electromagnetic measurement device operates at infrasonic wavelengths to collect unintended signatures from an implant embedded into said at least one biological implant recipient. In another embodiment the electromagnetic measurement device operates at X-ray wavelengths to collect unintended signatures from an implant embedded into said at least one biological implant recipient. In another embodiment said emissions measurement device operates from DC to optical wavelengths to collect unintended signatures from an implant embedded into said at least one biological implant recipient. In another embodiment said measurement device comprises a biologically analogous fixture to control for some of the factors present in vivo or in situ for projection to a realistic environment when said at least one electronic device is implanted in a biological host. In another embodiment said measurement device is capable of observing multiple electronic devices in a single active implant simultaneously. In another embodiment said measurement device is capable of diagnosing the state of degradation of multiple electronic devices in a single active implant simultaneously. In another embodiment said measurement device is capable of diagnosing the state of degradation of multiple electronic devices in at least one of a plurality of active implants in a number of biological situations related to a single biological host. In another embodiment said measurement device is capable of diagnosing the state of degradation of multiple implant electronics in at least one of a plurality of active implants in a number of biological situations in a plurality of hosts simultaneously. In another embodiment said measurement device is capable of predicting future degradation of multiple electronics in a single active implant simultaneously. In another embodiment said measurement device is capable of predicting future degradation of multiple electronics in at least one of a plurality of active implants in a number of biological situations related to a single biological host. In another embodiment said measurement device is capable of predicting future degradation of multiple implant electronics in at least one of a plurality of active implants in a number of biological situations in a plurality of biological hosts simultaneously. In another embodiment said measurement device is capable of assessing the risk of failure of multiple electronics in a single active implant simultaneously. In another embodiment said measurement device is capable of assessing the risk of failure of multiple electronics in at least one of a plurality of active implants in a number of biological situations related to a single biological host. In another embodiment said measurement device is capable of assessing the risk of failure of multiple implant electronics in at least one of a plurality of active implants in a number of biological situations in a plurality of biological hosts simultaneously.

In another embodiment the invention is a method to capture at least one of unintentional and intentional emissions from electronic devices implanted in a biological host, comprising: providing an emissions measurement device which comprises a data storage means, a receiver, and a processing means, collecting at least one electromagnetic emission from an implanted electronic device by means of said emission measurement device to create a set of collected electromagnetic emissions data, encoding said at least one electromagnetic emission, and storing said at least one encoded electromagnetic emission on said data storage means. In another embodiment the method further comprises creating a machine readable model from at least in part the at least one encoded electromagnetic emission. In another embodiment the set of collected electromagnetic emissions data represents or characterizes distinct electrical states, wherein the distinct electrical states are selected from the group comprising a nominal electronic function, a degraded electronic function, a failed electronic function and a combination thereof. In another embodiment the method further comprises translating said at least one electromagnetic emission, wherein said at least one electromagnetic emission is collected in a free-space environment, to mimic electromagnetic emissions that would pass through a biological tissue in vivo. In another embodiment the method further comprises providing a display, wherein the processing means determines a predictive risk assessment value derived from at least in part from the electromagnetic emission received by the receiver, and wherein the predictive risk assessment value is displayed by said display to a user. In another embodiment the method further comprises providing a display, wherein the processing means determines a predictive risk assessment value derived from at least in part from the electromagnetic emission received by the receiver, wherein the predictive risk assessment value is displayed by said display to a user, and wherein the set of collected electromagnetic emissions data represents or characterizes distinct electrical states, wherein the distinct electrical states are selected from the group comprising a nominal electronic function, a degraded electronic function, a failed electronic function and a combination thereof. In another embodiment the method further comprises validating an intended communication of the implanted electronic device. In another embodiment the method further comprises validating a radiation emission of the implanted electronic device. In another embodiment the method further comprises applying at least one algorithm for at least one encoded electromagnetic emission for the diagnosis of damage level and to predict failure of the implanted electronic device. In another embodiment the method further comprises a statistical signature database that is developed by measuring at least one of a plurality of signatures from at least one physical device. In another embodiment the method further comprises developing electronic device signatures by inducing varying levels of deleterious damage to an electronic device. In another embodiment the method further comprises correlating collected electromagnetic emissions data to a diagnosable feature of device health. In another embodiment the method further comprises applying at least one algorithm, comprising an array of modules automatically selected to determine a health characteristic of the implanted electronic device, to at least one encoded electromagnetic emission. In another embodiment the method further comprises providing a centralized database, wherein said centralized database uploads a set of information to the data storage means, wherein the set of information is selected from the group comprising an updated biological effect, an updated electronic signature, a specific biological situation information, a specific biological situation, a specific active implant's history and a combination thereof. In another embodiment the method further comprises providing a centralized database, wherein said centralized database receives a set of information from the data storage means, wherein the set of information is selected from the group comprising an updated biological effect, an updated electronic signature, a specific biological situation information, a specific biological situation, a specific active implant's history and a combination thereof. In another embodiment the method further comprises providing a centralized database, wherein said centralized database receives a set of information from the data storage means, wherein the set of information is selected from the group comprising an updated biological effect, an updated electronic signature, a specific biological situation information, a specific biological situation, a specific active implant's history, an observed electronics degradation modes, newly observed biological effects and a combination thereof, wherein personalized data is removed from the set of information before being received by said centralized database.

In another embodiment the invention is a method to encode and store collected unintentional and intentional emissions from electronic devices implanted in a biological host, comprising: providing a first emissions measurement device which comprises a first data storage means, a first receiver, and a first processing means, providing a second emissions measurement device which comprises a second data storage means, a second receiver, and a second processing means, collecting at least one electromagnetic emission from an implanted electronic device by means of said first emission measurement device to create a set of collected electromagnetic emissions data, encoding said at least one electromagnetic emission, and storing at least one encoded electromagnetic emission on said first data storage means. In another embodiment the method further comprises providing a centralized database, wherein said centralized database receives a set of information from the first data storage means, wherein said centralized database uploads the set of information to the second data storage means wherein the set of information is selected from the group comprising an updated biological effect, an updated electronic signature, a specific biological situation information, a specific biological situation, a specific active implant's history and a combination thereof. In another embodiment the method further comprises providing a centralized database, wherein said second data storage means uploads a set of information to the first data storage means, wherein said first data storage means receives a set of information from said second storage means, wherein the set of information is selected from the group comprising an updated biological effect, an updated electronic signature, a specific biological situation information, a specific biological situation, a specific active implant's history, an observed electronics degradation modes, newly observed biological effects and a combination thereof. In another embodiment the method further comprises sharing of at least one electromagnetic emission from the implanted electronic device between said first emissions measurement device and said second emission measurement device. In another embodiment the method further comprises sharing of at least one electromagnetic emission from the implanted electronic device between said first emissions measurement device and said second emission measurement device to enhance performance of the system.

In still another embodiment the invention is a system for analyzing electromagnetic emissions from an implanted electrical device, comprising: a receiver, an antenna electrically coupled to said receiver, a data processor, a data storage means, a set of collected electromagnetic emissions data, a model derived from said set of collected electromagnetic emissions data, wherein the processor determines at least one characteristic of an implanted electrical device, implanted in a biological host, through the application of the model to at least one signal received by the receiver related to an observed electromagnetic emission from the implanted electrical device. In another embodiment the set of collected electromagnetic emissions data represents or characterizes distinct electrical states. In another embodiment the set of collected electromagnetic emissions data represents or characterizes distinct electrical states, wherein the distinct electrical states are selected from the group comprising a nominal electronic function, a degraded electronic function, and a failed electronic function. In another embodiment the set of collected electromagnetic emissions data represents or characterizes distinct electrical states, wherein the distinct electrical states are selected from the group comprising a nominal electronic function, a degraded electronic function, a failed electronic function and a combination thereof. In another embodiment the set of collected electromagnetic emissions data represents or characterizes distinct electrical states for implantable electronics, wherein the distinct electrical states are selected from the group comprising a nominal electronic function, a degraded electronic function, a failed electronic function and a combination thereof. In another embodiment the set of collected electromagnetic emissions data represents or characterizes distinct electrical states for implanted electronics, wherein the distinct electrical states are selected from the group comprising a nominal electronic function, a degraded electronic function, a failed electronic function and a combination thereof. In another embodiment the set of collected electromagnetic emissions data represents or characterizes distinct electrical states for at least one component of said implanted electrical device, wherein the distinct electrical states are selected from the group comprising a nominal electronic function, a degraded electronic function, a failed electronic function and a combination thereof, and wherein the processor determines at least one characteristic of at least one component of the implanted electrical device through the application of the model to at least one signal received by the receiver related to an observed electromagnetic emission from the implanted electrical device. In another embodiment the model is in part derived from a knowledge of a biological situation related to said implanted electrical device. In another embodiment the processor determines a predictive risk assessment value at least in part from the at least one signal received by the receiver. In another embodiment the system further comprises a display, wherein the processor determines a predictive risk assessment value at least in part from the at least one signal received by the receiver, and wherein the predictive risk assessment value is displayed by said display to a user. In another embodiment the antenna functions at least in part in the near field to collect electromagnetic emissions from the implanted electrical device through at least one biological tissue layer. In another embodiment the set of collected electromagnetic emissions data comprises electromagnetic emissions data from implanted electronic devices and non-implanted electronic devices, and wherein the model correlates parallel histories of electromagnetic emissions data from implanted electronic devices and non-implanted electronic devices. In another embodiment the set of collected electromagnetic emissions data comprises electromagnetic emissions data from implanted electronic devices and non-implanted electronic devices, and wherein the model selects a relevant subset of data from the set of collected electromagnetic emissions data based on at least in part from a detected biological situation. In another embodiment the set of collected electromagnetic emissions data comprises electromagnetic emissions data from implanted electronic devices and non-implanted electronic devices, and wherein the model selects a relevant subset of data from the set of collected electromagnetic emissions data based on at least in part a characteristic of a detected active implant. In another embodiment the model is used to measure or diagnose at least one characteristic of the implanted electrical device to verify the implanted electrical device has not been tampered with.

In yet still another embodiment the invention is a system for analyzing electromagnetic emissions from an implanted electrical device, comprising: at least one receiver, an array of at least two antennas electrically coupled to said at least one receiver, a data processor, a data storage means, a set of collected electromagnetic emissions data, a model derived from said set of collected electromagnetic emissions data, wherein the processor determines at least one characteristic of an implanted electrical device through the application of the model to at least one signal received by the at least one receiver of an observed electromagnetic emission from the implanted electrical device. In another embodiment the set of collected electromagnetic emissions data represents or characterizes distinct electrical states. In another embodiment the set of collected electromagnetic emissions data represents or characterizes distinct electrical states, wherein the distinct electrical states are selected from the group comprising a nominal electronic function, a degraded electronic function, a failed electronic function and a combination thereof. In another embodiment said at least one receiver comprises at least two receivers each connected to a separate antenna of the array of at least two antennas. In another embodiment said at least one receiver comprises at least two receivers each connected to a separate antenna of the array of at least two antennas, and wherein each of said at least two receivers is configured to conduct a different signal processing approach on the at least one signal received by each of the at least two receivers. In another embodiment said at least one receiver comprises at least two receivers each connected to a separate antenna of the array of at least two antennas, and wherein the processor uses at least one algorithm to provide a diagnostic state of the implanted electrical device. In another embodiment the array of at least two antennas functions at least in part in the near field to collect electromagnetic emissions from the implanted electrical device through at least one biological tissue layer.

More broadly, the advantages of this invention are detection, diagnosis, monitoring, and prognosis of multiple active implants in the same biological host; detection diagnosis, monitoring, and prognosis of active implants to independently validate current built-in-test routines; decrease unnecessary explantation and provide guidance to medical professionals, biologists, and any life-sciences professional regarding the current and future state of active implants; monitor with finer granularity the interactions between biological situations and active implants and implant electronics over time; etc. These and many other advantages will become obvious to those skilled in the art and should not be construed as describing all the advantages or limiting the advantages of the present invention; rather, the scope and spirit of the present invention's advantages should be construed as widely as is possible.

OBJECTS OF THE INVENTION

It is therefore an object of the invention to extract relevant information from an observed unintentional electromagnetic emission from an electrically enabled device implanted in or attached to a biological host or system.

It is also an object of the invention to detect electrically enabled devices implanted in or attached to biological hosts or systems.

It is an object of the invention to identify electrically enabled devices implanted in or attached to biological hosts or systems.

Another object of the invention is to locate electrically enabled devices implanted in or attached to biological hosts or systems.

A further object of the invention is to detect various states of functionality or degradation of electrically enabled devices implanted in or attached to biological hosts or systems.

Still another object of the invention is to discriminate between various states of functionality or degradation of the electronics located in electrically enabled devices implanted in or attached to biological hosts or systems.

Yet another object of the invention is to diagnose various states of functionality or degradation of electrically enabled devices implanted in or attached to biological hosts or systems.

It is an object of the invention to predict the course and timeframe of functional degradation of electrically enabled devices implanted in or attached to biological hosts or systems.

Another object of the invention is to assess the risk of functional degradation of electrically enabled devices implanted in or attached to biological hosts or systems.

A further object of the invention is to predict the timeframe of failure of electrically enabled devices implanted in or attached to biological hosts or systems.

Yet another object of the invention is to assess the risk of failure of electrically enabled devices implanted in or attached to biological hosts or systems.

It is an object of the invention to provide a diagnostic and prognostic method and apparatus that is enhanced by complementary indicators of states of repair of electrically enabled devices implanted in or attached to biological hosts or systems.

A further object of the invention is to provide a diagnostic and prognostic method and apparatus that is enhanced by complementary indicators of the risk and timeframe of failure of electrically enabled devices implanted in or attached to biological hosts or systems.

Yet another object of the invention is to provide a diagnostic and prognostic method and apparatus that is enhanced by complementary indicators of the risk and timeframe of functional degradation of electrically enabled devices implanted in or attached to biological hosts or systems It is an object of the invention to wirelessly and noninvasively diagnose various states of repair of electrically enabled devices implanted in or attached to biological hosts or systems for the purpose of tracking animals without the need for recapture.

Another object of the invention is to noninvasively diagnose various states of repair of electrically enabled devices implanted in or attached to biological hosts or systems for the purpose of medical treatment.

A further object of the invention is to broadly expand current active implant monitoring paradigms by providing more comprehensive assessments of the state of repair of implant electronics in active implants.

Yet another object of the invention is to improve long term outcomes for active implant patients.

It is another object of the invention to accomplish the other objects of the invention by receiving emissions generated by electrically enabled devices implanted in or attached to biological hosts or systems through plant walls, human tissue, or any other form of biological tissue.

Still another object of the invention is to accomplish the other objects of the invention by receiving emissions generated by electrically enabled devices implanted in or attached to biological hosts or systems and affected in any way by plant walls, human tissue, or any other form of biological tissue.

It is an object of the invention to extract relevant information from an observed unintentional electromagnetic emission from an electrically enabled device implanted in or attached to a biological host or system.

Another object of the invention is to provide a diagnostic and prognostic method and apparatus that is enhanced by a database of known biological effects on electromagnetic emissions.

A further object of the invention is to provide a diagnostic and prognostic method and apparatus that is enhanced by a database of known active implant component history models.

Yet another object of the invention is to provide a diagnostic and prognostic method and apparatus that is enhanced by a database of known active implant subsystem history models.

It is an object of the invention to provide a diagnostic and prognostic method and apparatus that is enhanced by a database of known active implant device history models.

It is an object of the invention to provide a diagnostic and prognostic method and apparatus that is enhanced by a database of biological host specific active implant device history models.

Another object of the invention is to provide a diagnostic and prognostic method and apparatus that is enhanced by a database of individual host (e.g., patient) specific active implant device history models.

A further object of the invention is to provide a diagnostic and prognostic method and apparatus that is enhanced by a database of biological specimen specific active implant device history models.

Yet another object of the invention is to provide a diagnostic and prognostic method and apparatus that is enhanced by a software-updatable master database of active implant device history models.

Another object of the invention is to provide a diagnostic and prognostic method and apparatus that is enhanced by distributed client databases of active implant device history models that provide updates a centralized, software-updatable master server database of active implant device history models.

A further object of the invention is to provide a diagnostic and prognostic method and apparatus that is enhanced by distribution of continually updated electronic implant device history models to client databases in an automated fashion.

Yet another object of the invention is to provide a diagnostic and prognostic method and apparatus that is enhanced by the transfer of specific device history between client databases of specific device history models to allow for changes in geography of biological hosts.

It is an object of the invention to provide a method and apparatus that is enhanced by updating local and master device degradation models based on newly discovered degradation modes.

A further object of the invention is to measure, diagnose, and validate the functional state of an active implant using at least one of the implant electronics' unintended or intended emissions during manufacturing, sterilization, and quality control independently of other built in tests.

Still another object of the invention is to create a baseline signature of an active implant using at least one of the implant electronics' unintended or intended emissions after manufacture to begin tracking the active implant and implant electronics.

Yet another object of the invention is to measure and diagnose the state of the active implant and implant electronics using at least one of the implant electronics' unintended or intended emissions at the implantation facility to compare with the post-manufacturing emissions to verify that the implant remains fully functional.

It is an object of the invention is to measure and diagnose the state of the active implant and implant electronics using at least one of the implant electronics' unintended or intended emissions at the implantation facility to compare with the post-manufacturing emissions to verify that the implant has not been tampered with.

A further object of the invention is to measure and diagnose the state of the active implant and implant electronics using at least one of the implant electronics' unintended or intended emissions to verify device integrity prior to implantation.

Still another object of the invention is to create a baseline signature of an active implant using at least one of the implant electronics' unintended or intended emissions immediately after implantation.

Yet another object of the invention is to measure and diagnose the state of the active implant and implant electronics using at least one of the implant electronics' unintended or intended emissions immediately post implantation to validate the implant electronics' functionality.

It is an object of the invention is to measure and diagnose the state of the active implant and implant electronics using at least one of the implant electronics' unintended or intended emissions immediately post implantation to create a baseline signature of an active implant in its desired biological situation.

A further object of the invention is to monitor, diagnose, and predict the state of the active implant and implant electronics using at least one of the implant electronics' unintended or intended emissions periodically throughout the device's lifetime.

Still another object of the invention is to monitor, diagnose, and predict the state of an active implant and implant electronics using at least one of the implant electronics' unintended or intended emissions during device degradation or failure.

Yet another object of the invention is to measure and diagnose the state of the active implant and implant electronics using at least one of the implant electronics' unintended or intended emissions after explantation.

It is an object of the invention is to measure and diagnose the state of the active implant and implant electronics using at least one of the implant electronics' unintended or intended emissions during post failure testing.

Yet another object of the invention is to detect implanted electronics for patients who are unresponsive and unable to share appropriate information with medical providers.

Still yet another object of the invention is to detect damage to implanted electronics that occur during medical procedures such as MRIs, CT scans electric and electromagnetic endoscopy.

BRIEF DESCRIPTION OF THE DRAWINGS

In drawings which illustrate a several preferred embodiments of the invention.

DETAILED DESCRIPTION OF THE INVENTION

Figure 1:
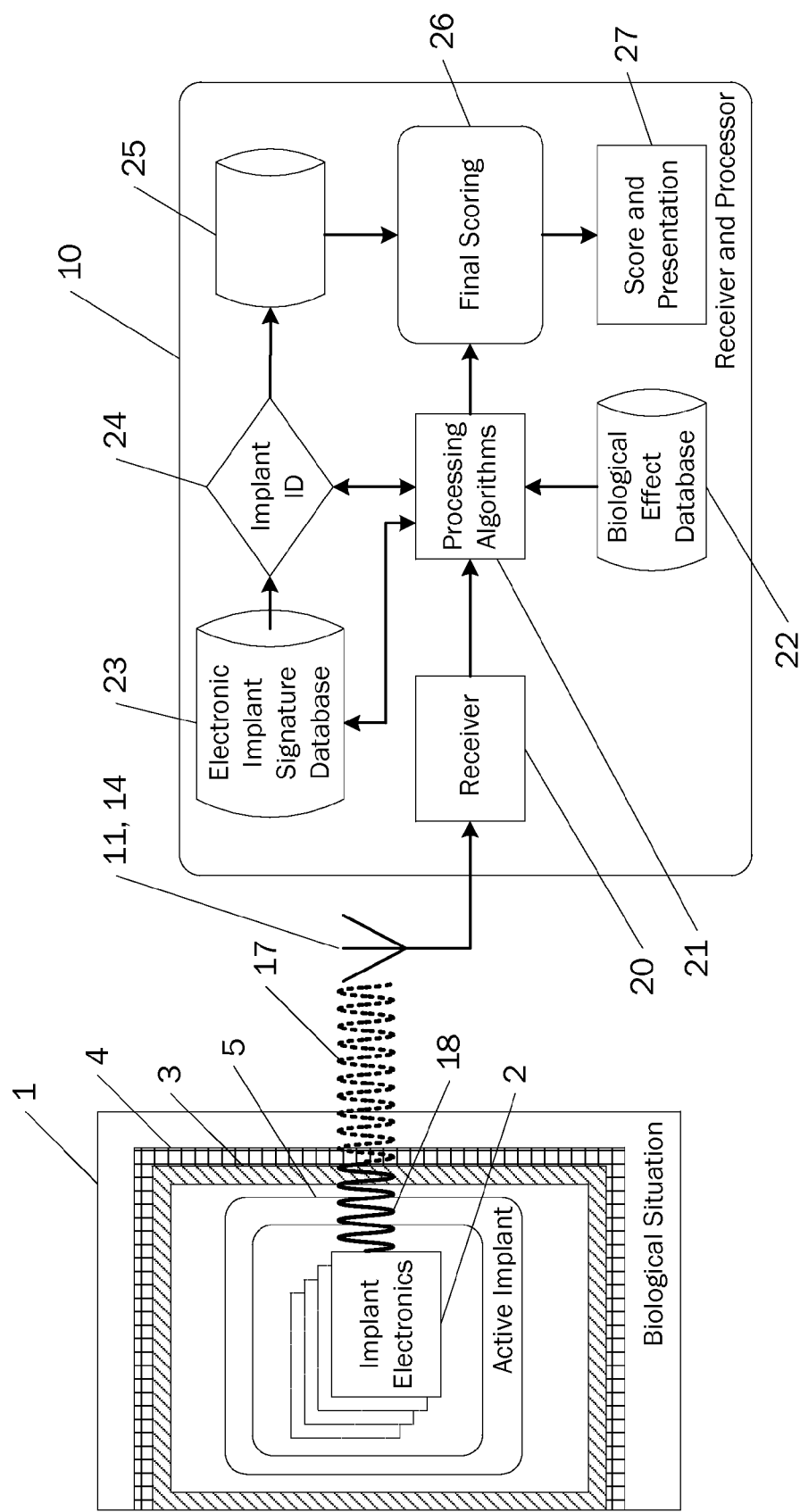
FIG. 1 is a schematic diagram of the apparatus of the invention for detecting, identifying, and/or locating electrically enabled devices implanted in or attached to biological hosts/systems; discriminating between and diagnosing various states of electrically enabled devices implanted in or attached to biological hosts/systems; and predicting or prognosticating the course and timeframe of function, degradation, or failure of electrically enabled devices implanted in or attached to biological hosts/systems.

For simplicity and clarity, the term active implant shall mean any electrically enabled device or system implanted in or attached to a biological host or system. The term biological situation shall mean the relative location, placement, or residency of the active implant within or on the biological host or system. The term implant electronics shall mean the electronics or subset thereof enabling an active implant to function. The term electronic device shall not be limited to devices intended to be implants, but should encompass all electronic and electrical devices. The term emissions measurement device shall mean any device capable of measuring electromagnetic emissions and re-emissions. An intentional emission shall mean a electromagnetic emission that is intentionally generated or directed to an intended target. An unintentional emission shall mean all other electromagnetic emissions. Emissions or electromagnetic emissions shall mean all and any electromagnetic emissions.

Prior to proceeding to the more detailed description of the present invention it should be noted that, for the sake of clarity and understanding, identical components which have substantially identical functions have been identified with identical reference numerals throughout the several views illustrated in the drawing figures.

DESCRIPTION OF FIGURE ELEMENTS FOR A FIRST ENVISIONED EMBODIMENT

Referring now to the invention in more detail, in FIG. 1, FIG. 2, FIG. 5, and FIG. 8 there is shown a signal processor 10 that collects at least one of the intentional emissions 12 and unintentional emissions 13 emitted by substantially all electronic devices regardless of implantation in or attachment to any biological host. One or more of the intentional emissions 12 and unintentional emissions 13 make up generated emissions 18 that are influenced by biological situation 1 and become raw emissions 17.

Referring to FIG. 1, FIG. 2, FIG. 3, FIG. 5, and FIG. 7 there is shown active implant 5 that is another object of this invention. Implant electronics 2, integral to active implant 5, are the ultimate source of raw emissions 17 from which information is extracted to accomplish the goals of this invention.

Figure 2:
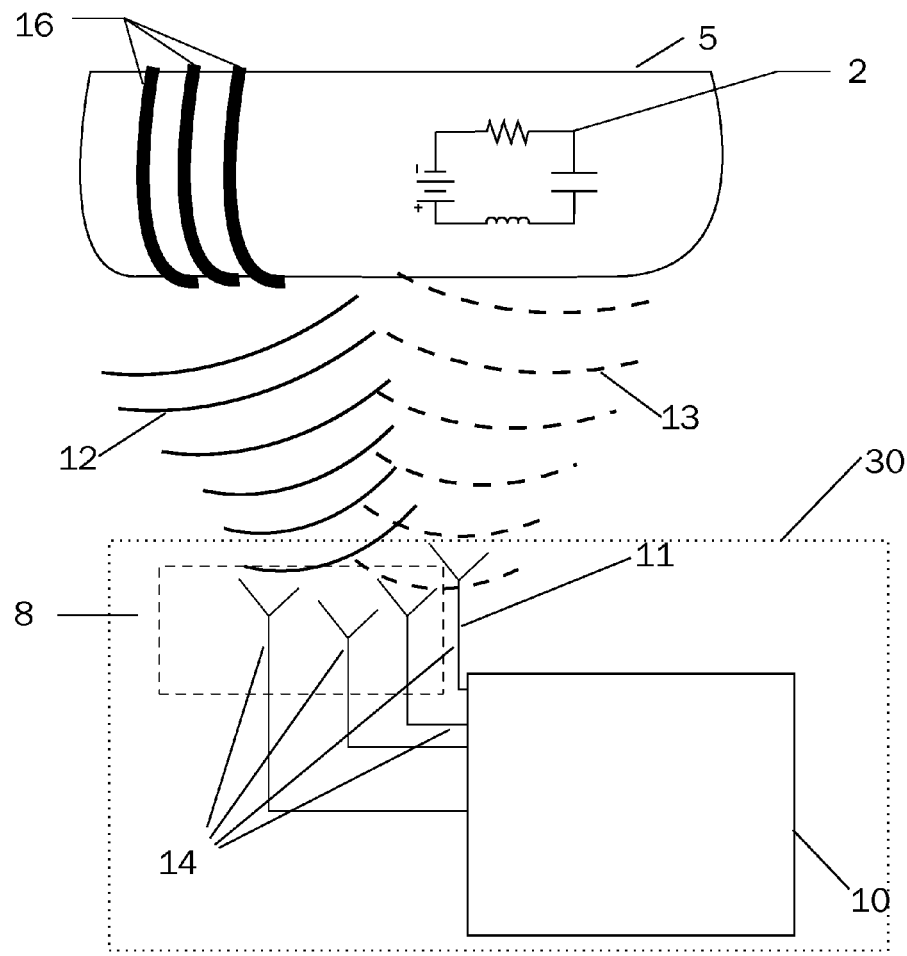
FIG. 2 is a schematic diagram illustrating an envisioned embodiment of the invention harvesting electromagnetic emissions from a representation of an electrically enabled device implanted in or attached to a biological host or system.
Figure 3:
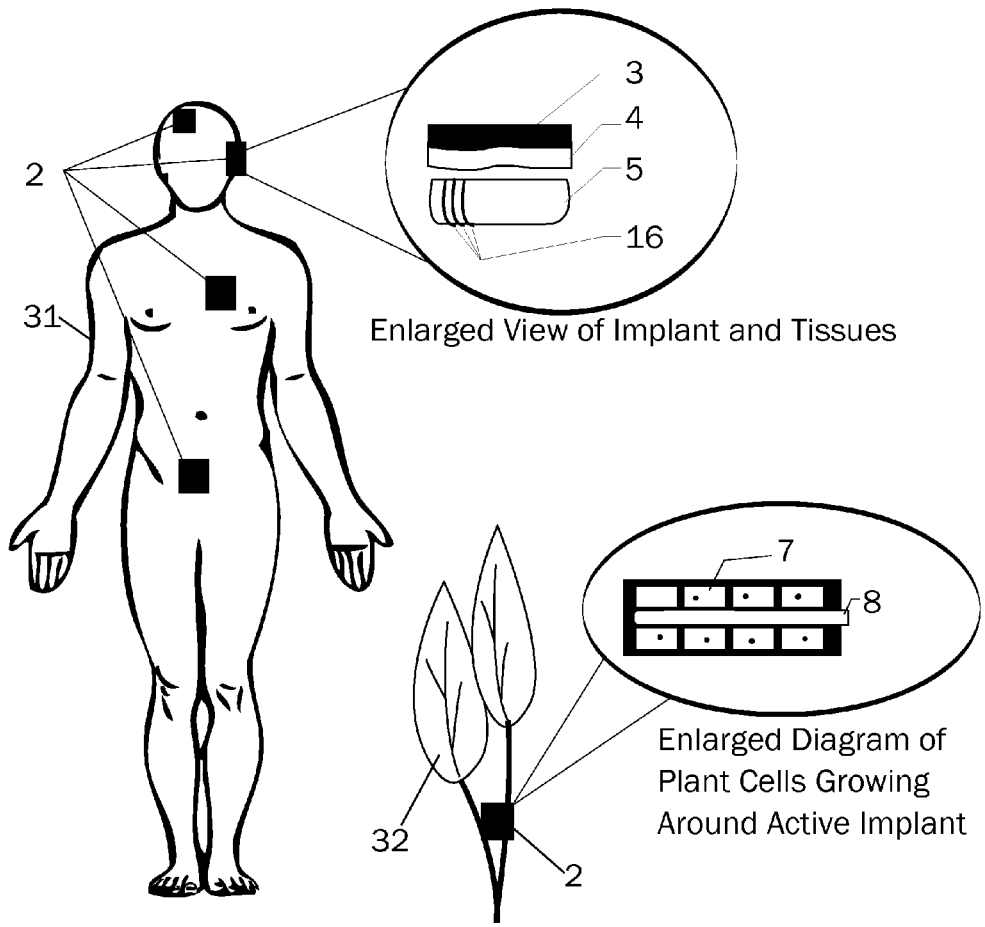
FIG. 3 is an illustration of several representative biological situations in which electrically enabled devices are implanted in or attached to biological hosts or systems.

Said raw emissions 17, shown in FIG. 1 and FIG. 2, are the results of generated emissions 18 interacting with one or more of first tissue 3, second tissue 4, and plant tissue 7 shown in FIG. 1 and FIG. 3. Said generated emissions will be influenced by the biological situation 1 shown in FIG. 1 and exemplified in FIG. 3 through FIG. 5, and FIG. 8.

Figure 4:
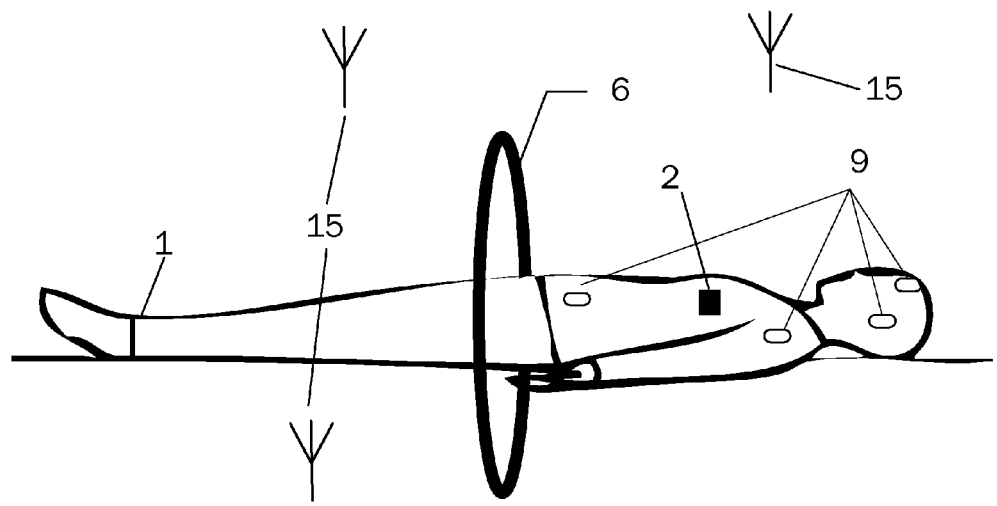
FIG. 4 is an illustration of several representative locations of envisioned embodiments of receiving antenna(s) that are utilized to harvest the electromagnetic emissions from electrically enabled devices that are implanted in or attached to a representative biological host.

Also in FIG. 1, there is shown the receiving antenna(s) 14. Antenna(s) 14 can be separated into a required antenna 11 and optional receiving antenna(s) 8 as shown in FIG. 2, and can comprise without limitation or exclusivity, one or more dipole antennas 15, conformal antennas 9, loop antennas 6, or any other antenna type as shown in FIG. 4.

Also in FIG. 1, there is shown an example embodiment of the functionality used to accomplish the objects of this invention. This embodiment comprises an EM receiver 20 that receives said raw emissions 17 from the receiving antenna 14, extracts and filters components of interest, and passes these components to the processing algorithms 21. Said processing algorithms compare the components of interest to one or both of the biological effect database 22 and the electronic implant signature database 23 and attempt to identify the implant. Upon implant identification 24, the processing algorithms 21 further transmit the extracted information to final scoring 26. Final scoring 26 then utilizes this information along with component, subsystem, and device history models 25 to generate a score that is presented to the user through the score and presentation 27.

In further detail, while still referring to the invention of FIG. 1, FIG. 2 is a schematic diagram illustrating an envisioned embodiment of the invention apparatus 30 harvesting or collecting electromagnetic emissions from implant electronics 2 located in active implant 5, an electrically enabled device implanted in or attached to a biological host or system. The invention apparatus 30 is instantiated in FIG. 2 by an embodiment of the invention comprising the signal processor 10 and receiving antenna(s) 14. As previously mentioned, receiving antenna(s) 14 can be separated into a required antenna 11 and optional receiving antenna(s) 8. These antennas can be in any configuration, or of any type to extract useful information from at least one of the unintentional emissions 13 and intentional emissions 12. While intentional emissions 12 can be evoked by implant electronics 2 and transmitted via intentional implant antenna 16, unintentional emissions 13 may, but are not necessarily directly transmitted by implant antenna 16.

In further detail, still referring to the invention of FIG. 1, FIG. 3 is an illustration of several locations implant electronics 2 may, without limitation, be found in a biological host, biological system or a portion of or combination thereof. For example, human biological situation 31 shows potential, but not limiting, locations of implant electronics 2 associated with active implant 5 placement, including, but not limited to, locations associated with cochlear implants, vagal nerve stimulators, bladder stimulators, intracardial devices, or pacemakers. Any active implant 5 in a human biological simulation 31 must be associated with biological tissue in some way as is represented by the proximity of active implant 5 and implant antenna 16 to first tissue 3 and second tissue 4. This proximity and the intrinsic composition of at least one of first tissue 3 and second tissue 4 will affect active implant 5's emissions, either because of the change induced by at least one of first tissue 3 and second tissue 4 on electromagnetic propagation parameters or because the interface between at least two of first tissue 3, second tissue 4, free space inside or outside the biological host or system, implant 5, or implant antenna 16 will affect the character and propagation of any emissions from which information may be extracted.

Still referring to FIG. 3, plant biological situation 32 shows an example location of implant electronics 2 and the mechanical contact between plant tissue 7 and active implant component 28 that could affect the emissions emanating from the implant electronics 2. Other example factors that could affect emissions and for which the present invention would correct could be the plant tissue 7 intrinsic composition, the interface between individual cells within plant tissue 7, or between plant tissue 7 and free space inside or outside the biological host or system.

Figure 5:
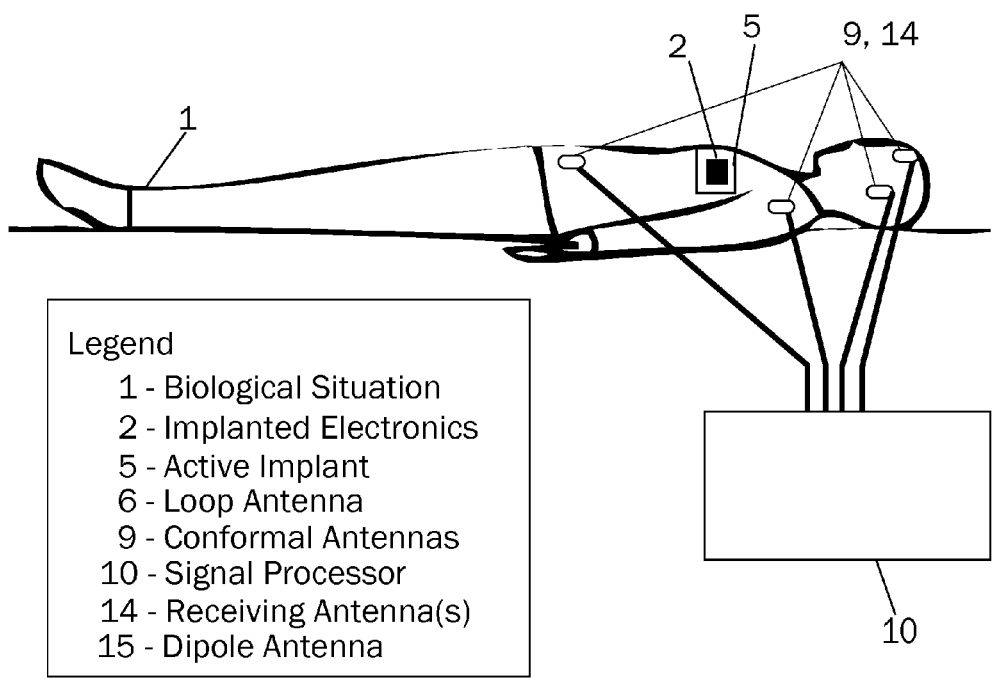
FIG. 5 is an illustration of a possible use of an example embodiment of the apparatus of the present invention.

In further detail, still referring to the invention of FIG. 1, FIG. 4, without loss of generality of antenna type, placement, orientation, etc., illustrates several representative locations and envisioned embodiments of receiving antenna(s) that can be utilized to harvest electromagnetic emissions from implant electronics 2 in any given biological situation 1. Dipole antennas 15, are represented in an array configuration in free space, conformal antennas 9 are represented as attached to the biological host's body either permanently, semi-permanently, or temporarily using a variety of (preferably non-damaging) means, and a loop antennas 6 is represented as a preferable embodiment as they are well suited to receive lower frequency emissions which are preferentially transmitted through biological tissues. Referring to FIG. 5, several attached conformal antennas 9 are used as receiving antennas 14 and feed signal processor 10 as a part of the present invention's objective of identifying, diagnosing, and making a prognosis for implant electronics 2, and by extension active implant 5.

Figure 6:
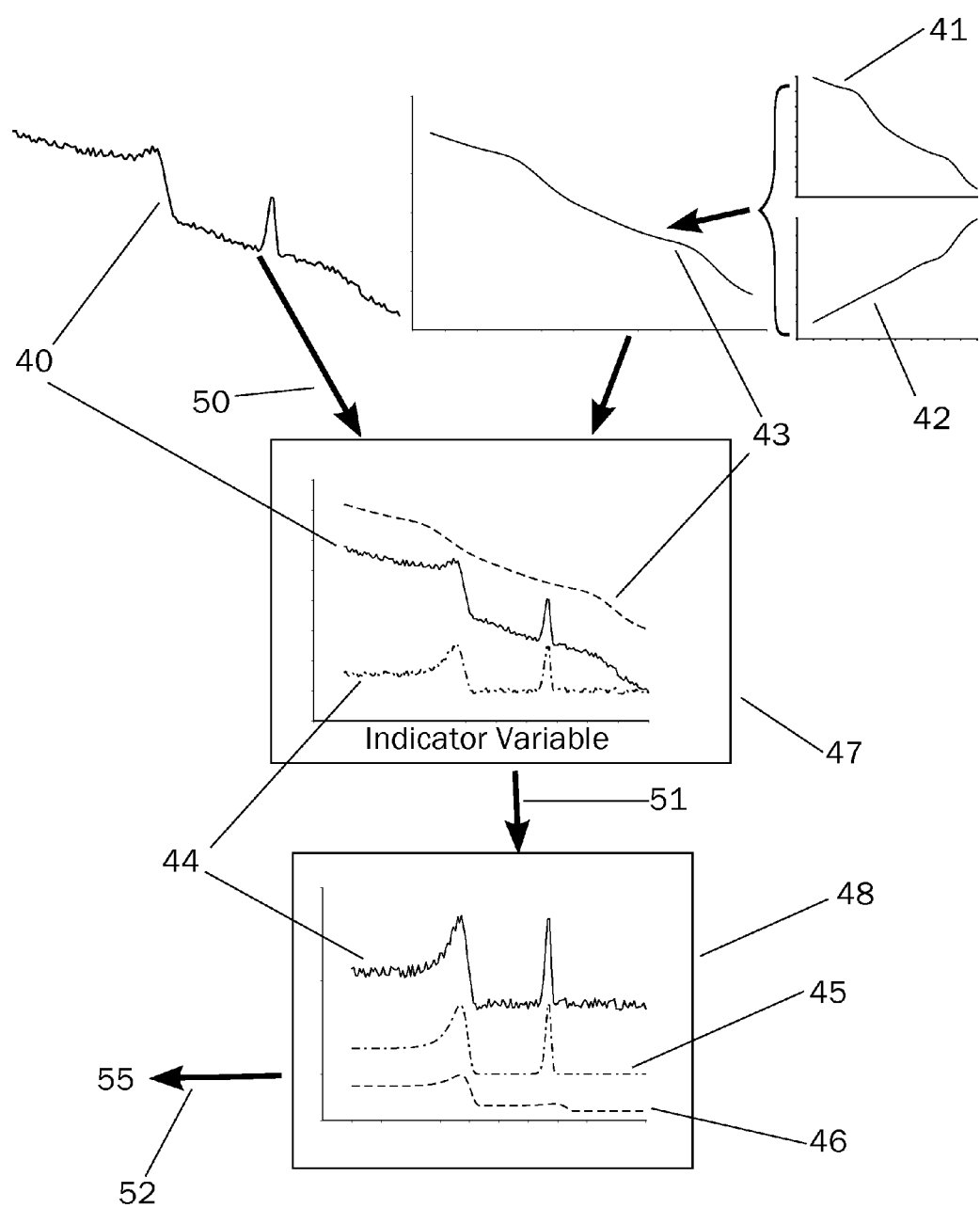
FIG. 6 is a schematic diagram representing a method of processing of received signatures using any a priori or detected information about known biological host/system induced effects to remove biologically induced artifacts.

While still referring to FIG. 1, refer now to FIG. 6, a schematic diagram representing an example of a method of processing raw emissions 17 using any a priori or detected information about known biological host/system induced effects to remove biologically induced artifacts and then diagnose and predict the state of the implant electronics. Raw emissions 17 are encoded into received data 40 that is then is passed into biological effect remover 47. Using a priori or detected knowledge about the target active implant, corresponding implant electronics, or the implant's biological situation, the method combines at least one of first biological effect characteristic 41 and second biological effect characteristic 42 to generate composite biological situation effect characteristic 43. Biological effect remover 47 then utilizes a variety of signal processing algorithms to extract indicator data 44 from received data 40 based upon the composite biological situation effect characteristic 43. Indicator data 44 is then passed to implant diagnostic unit 48. Component, subsystem, and device history models 25 comprising nominally functioning implant signature 45 and aged implant signature 46 are utilized to derive diagnostic and prognostic information 55 in conjunction with indicator data 44 about implant electronics 2, and by extension active implant 5. The diagnostic and prognostic information 55 is then passed on to any additional scoring or presentation. Pre-biological effect removal processing 50, post-biological effect removal processing 51, or post-diagnostic and prognostic processing 52 may be used to identify components, subsystems, or complete active implants, as well as feed back or forward into any stage of the diagnostic process along with any a priori information that becomes a relevant input to the next stage of processing.

DESCRIPTION OF FIGURE ELEMENTS FOR A SECOND ENVISIONED EMBODIMENT

Figure 7:
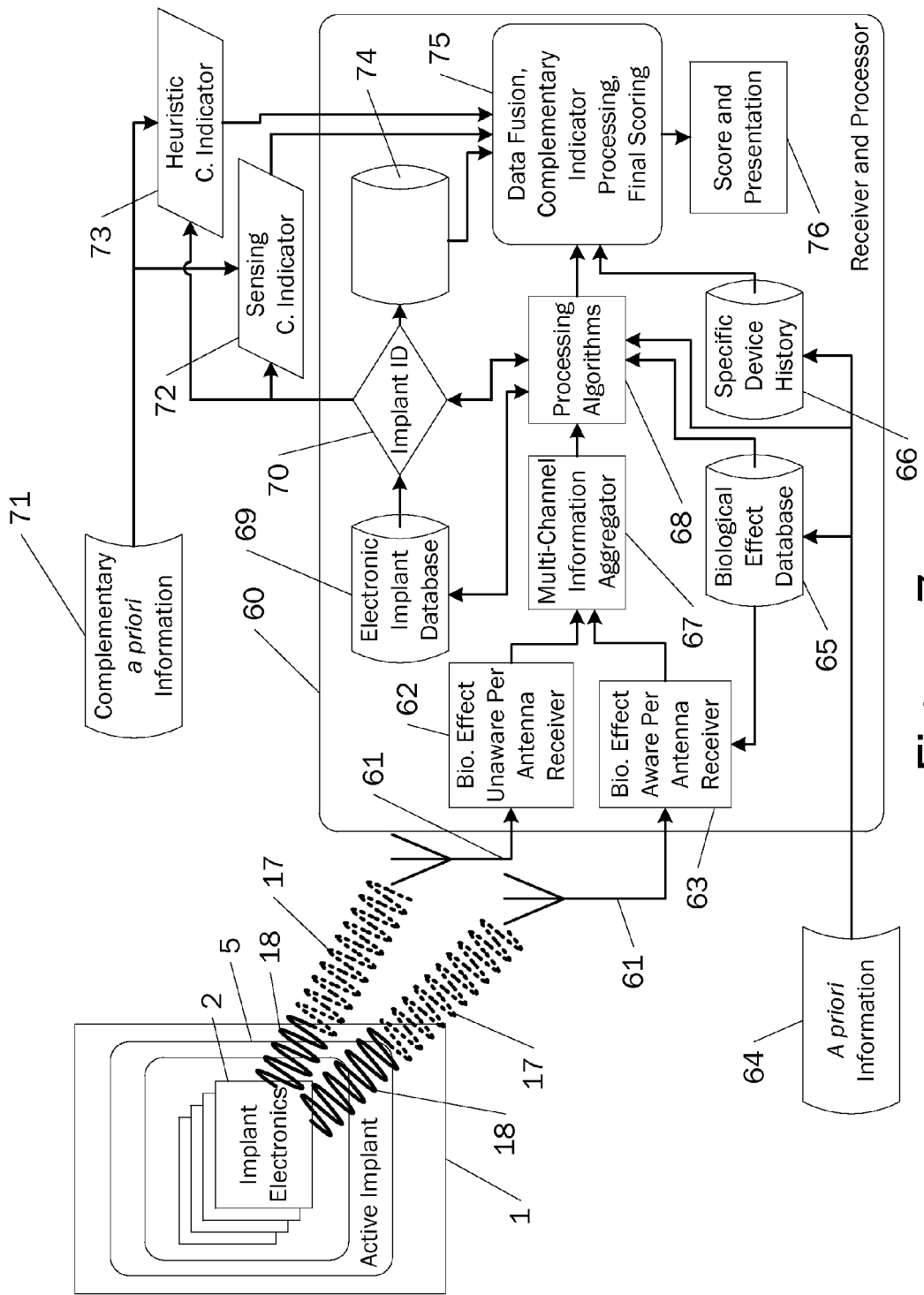
FIG. 7 is a schematic diagram of an envisioned embodiment of the apparatus of the invention and a flow chart of an envisioned embodiment of the method of the invention.

Referring now to the invention in more detail, in FIG. 7 is shown second embodiment of means to accomplish the objects of this invention. Still referring to FIG. 7, there is shown local signal processor 60, antenna array 61 comprising (without limitation) two complementary antennas attached to non-biological host aware per antenna receiver 62 and biological host aware per antenna receiver 63. Biological host aware per antenna receiver 63 is informed by biological effect data stored in biological effect database 65 and selected by a priori information 64 to eliminate biological effects induced by biological situation 1. The output of non-biological host aware per antenna receiver 62 and biological host aware per antenna receiver 63 is combined into the input of local multi-channel information aggregator 67. Multi-channel information aggregator 67 combines the output of non-biological host aware per antenna receiver 62 and biological host aware per antenna receiver 63 and passes unified, aggregate information to local processing algorithms 68. Said local processing algorithms 68 utilize a priori information 64 to correlate the components of interest with biological effect data stored in biological effect database 65 and selected by a priori information 68 as well as to select candidate active implant types stored in local active implant database 69 to pass on to implant identification engine 70.

Still referring to FIG. 7, implant identification engine 70 selects the appropriate implant type from said candidate active implant types in conjunction with the processed data from local processing algorithms 68 and uses it to select the appropriate component, subsystem, and device history models from component, subsystem, and device history model database 74 which are passed on to data fusion, complementary indicator processing, and final scoring 75. Implant identification engine 70 also sends the implant identification type to any external complementary indicators such as sensing indicator 72 or heuristic complementary indicator 73. One or both of sensing indicator 72 or heuristic indicator 73 may utilize as input any number of diagnostic methods or any amount of complementary a priori information 71.

Data fusion, complementary indicator processing, and final scoring 75 receives as input the output from sensing complementary indicator 72, heuristic complementary indicator 73, component, subsystem, and device history model database 74, local processing algorithms 68, and specific device history database 66. Output from specific device history database 66 is selected by a priori information 64. Data fusion, complementary indicator processing, and final scoring 75 extracts a selection of relevant indicators and resolves any conflicting indicators before passing a finalized score and presentation to score and presentation unit 76.

Figure 8:
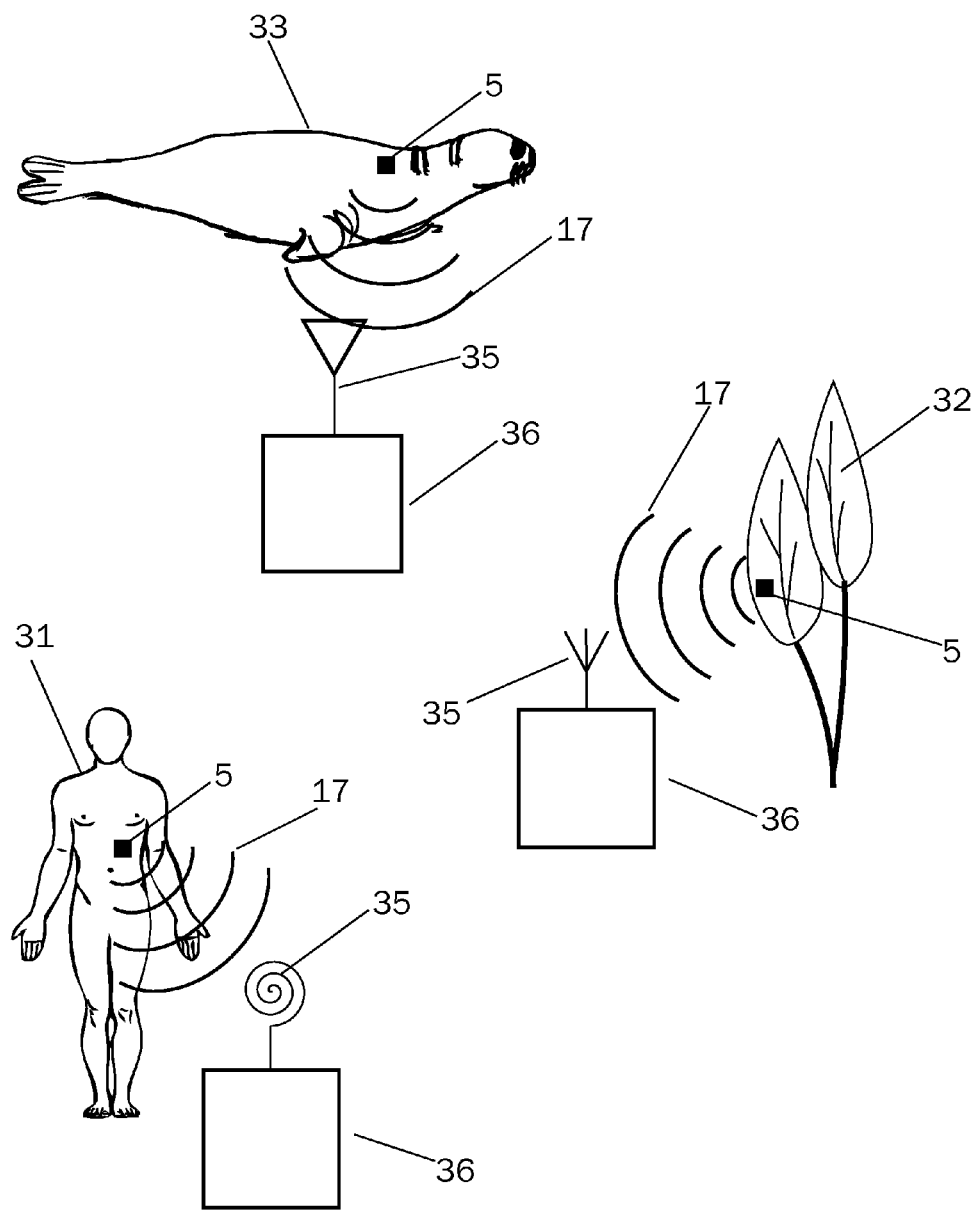
FIG. 8 is an illustration of a possible use of an envisioned embodiment of the invention used in a field configuration to diagnose multiple electrically enabled devices implanted in or attached to biological hosts/systems.

Now referring to FIG. 8, the construction details of the diagnostic targets of the invention as shown in FIGS. 1 to 7 are described in human biological situation 31, plant biological situation 32, and animal biological situation 33 in FIG. 2 and FIG. 8. This shows that a single apparatus 36 may be applied to various biological situations using at least one or more interchangeable antennas, near field probes, or any other electromagnetic probes 35 depending on the characteristics of active implant 5's biological situation.

Figure 9:
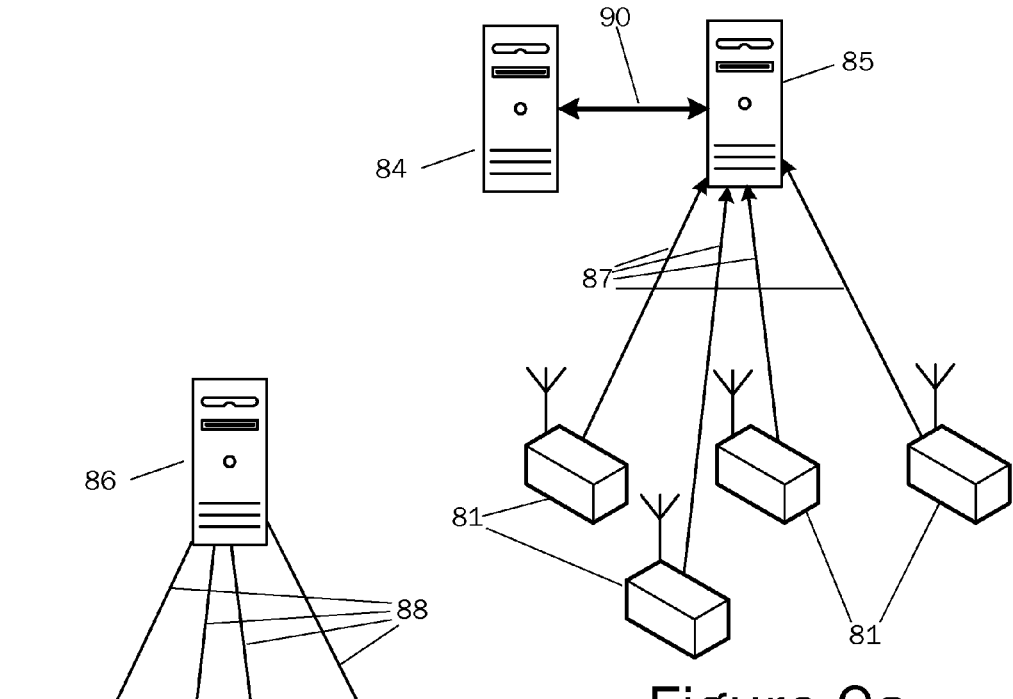
FIG. 9 is a schematic diagram of an envisioned embodiment of the invention demonstrating a subset of the invention's communication capabilities and modalities.
Figure 9:
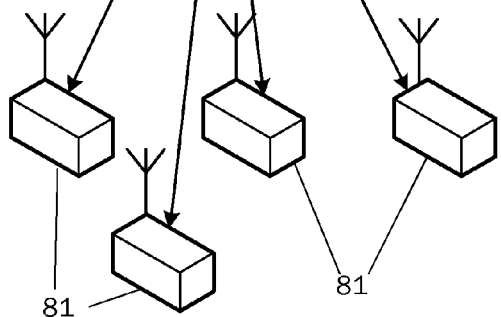
Figure 9:
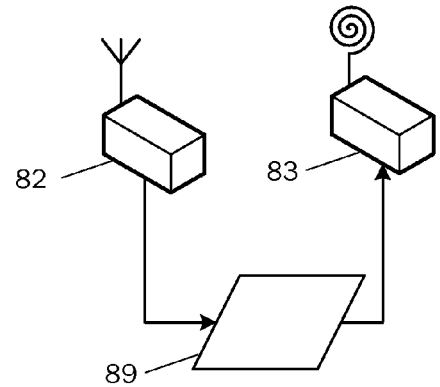

Now referring to FIG. 9a, one of a plurality of first client invention embodiment 81 transfers a parameter or novel datum included in at least one of biological effect database 22, device history models 25, biological effect database 65, specific device history database 66, component, subsystem, and device history model database 74 of FIG. 1 and FIG. 7 or any other relevant sets of data along with at least one datum comprising at least one of a corresponding score generated by scoring mechanism 26, corresponding implant identification generated by implant identification 24, implant signature from electronic implant signature database 23, local active implant database 69, implant identification token generated by implant identification engine 70, and final score generated by data fusion, complementary indicator processing, and final scoring 75 of FIG. 1 and FIG. 7 or any other indicator to a centralized or semi-centralized data collection server 85 via at least one of a plurality of incoming communication channels 87. The data is aggregated at the collection server 85 and the aggregated data is transferred for further processing to processing server 84 via two way link 90.

Referring now to FIG. 9b, transmission server 86 sends parameters, models, and data derived from the novel information by the processing server 84 of FIG. 9a to at least one of first client invention embodiment 81 via at least one of a plurality of outgoing communication channels 88. The parameters, models, and data can be incorporated into at least one of biological effect database 22, device history models 25, biological effect database 65, specific device history database 66, component, subsystem, and device history model database 74 of FIG. 1 and FIG. 7 or any other relevant methods and units.

Referring now to FIG. 9c, at least one of a plurality of individual records 89 including at least one of device specific and biological situation specific data can be transferred to from source client invention embodiment 82 to target client invention embodiment 83 via at least one of a plurality of communication channels or mass storage devices.

Figure 10:
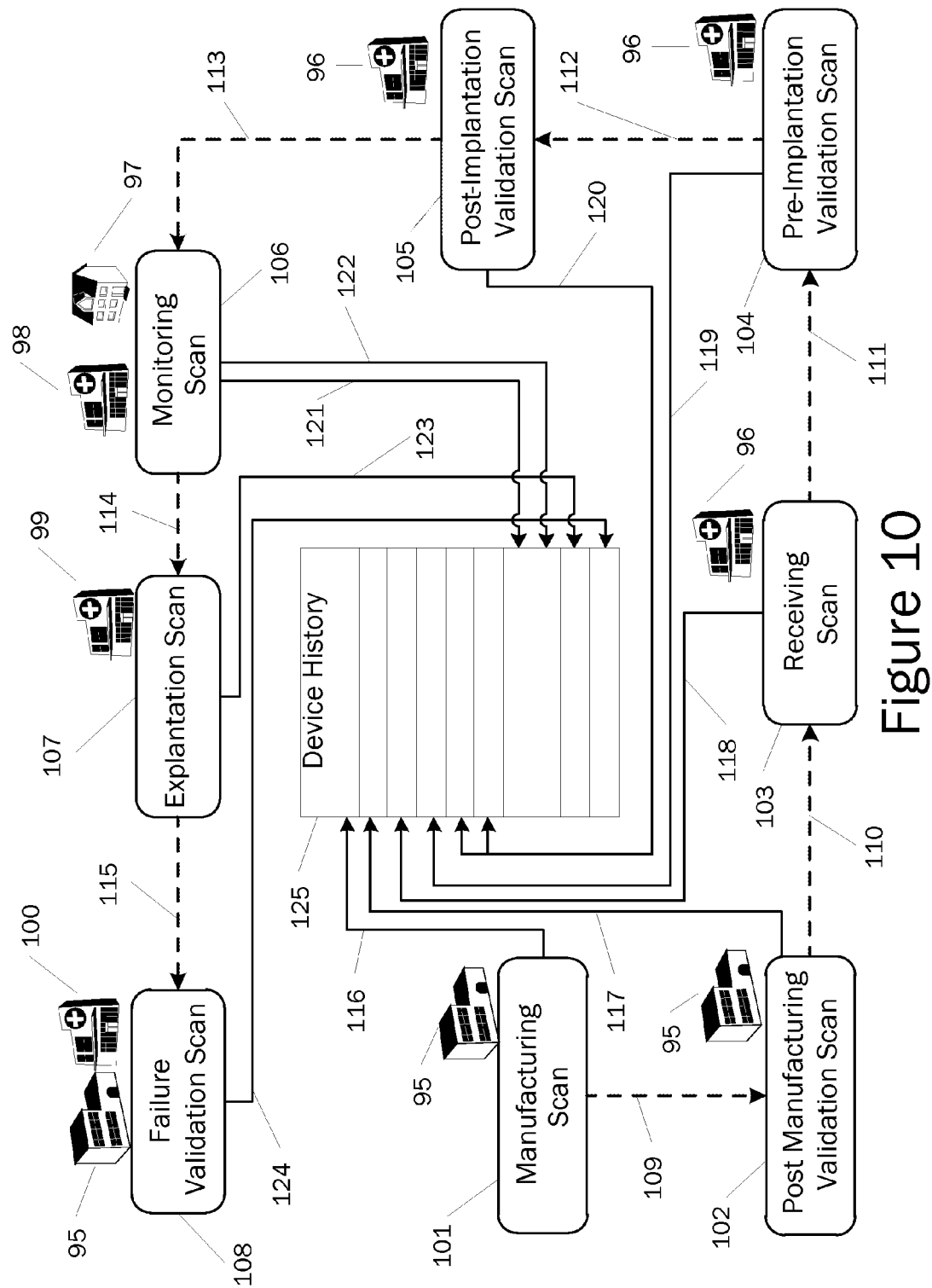
FIG. 10 is a schematic diagram of an envisioned lifecycle of an active device and its associated history as generated by the present invention as it passes from manufacture through its useful life to end-of-life and disposal.

Referring now to FIG. 10, the present invention in several embodiments begins monitoring an active implant during manufacture 101 in implant manufacturing facility 95 and begins the device signature history 125 with manufacturing emissions profile 116 comprising machine readable, encoded, and untransformed electronic emissions. Upon completion of manufacturing said active implant passes through sterilization and packaging 109.

Still referring to FIG. 10, the present invention then preferably diagnoses the active implant during post-manufacturing validation 102, again in implant manufacturing facility 95 and compares the post-manufacturing emissions profile 117 comprising machine readable, encoded, and untransformed electronic emissions with manufacturing emissions profile 116 to detect any discrepancies that might indicate degradation. Post-manufacturing emissions profile 117 is then stored in device signature history 125. Said active implant is shipped to implanting hospital 96 and accepted by receiving.

Continuing to refer to FIG. 10, during receiving scan 103, any discrepancies that may have been introduced during shipping 110 are noted by comparing and contrasting hospital receiving emissions profile 118 with the implant electronics model encoded by data stored in device signature history 125. After passing receiving scan 103, said active implant is placed in storage 111 and transported throughout the implanting hospital 96 to the implantation area. To verify that said implant has not been tampered with or damaged while in storage 111, a pre-implantation validation scan 104 is conducted and the pre-implantation emissions profile 119 is validated against the implant electronics model and device signature history 125. If the device passes pre-implantation validation scan 104, then the device is implanted into the patient. A post-implantation validation scan 105 is then performed just prior to or just after completing implantation 112; both operations are performed in implanting hospital 96. The data from post-implantation validation scan 105 then becomes part of device signature history 125. It is important to note that post-implantation validation scan 105 is the first scan that measures a signature comprising both biological situation induced effects as well as electronic induced effects. Given this, post-implantation emissions profile 120 can be separated into a composite post-implantation device signature and a biological situation signature that can be stored separately in device signature history 125, using a composite biological host-implant electronics model derived from data previously stored (i.e., manufacturing emissions profile 116, post-manufacturing emissions profile 117, hospital receiving emissions profile 118, and pre-implantation emissions profile 119). Said active implant is then released, internal to the patient to fulfill its intended purpose.

Still referring to FIG. 10, upon patient release 113 from implanting hospital 96, the implant begins to fulfill its intended purpose and is subjected to at least one of a plurality of periodic monitoring scans 106. The scans can be performed (without limitation) in patient home 97, monitoring clinic 98, or any other location where the present invention can be located. During periodic monitoring scans 106, composite periodic monitoring emission profile 121 is compared to a composite biological host-implant electronics model based on the previous information stored in device signature history 125, a prognostic value is reported, and composite periodic monitoring emission profile 121 is subsequently appended to device signature history 125. Periodic monitoring scans 106 then continue to add a plurality of additional composite periodic monitoring emission profiles 121 to device signature history 125. Provided the biological host lifetime exceeds that of the active implant useful lifetime, at least one of periodic monitoring scans 106 can measure and confirm significantly degraded emission profile 122 that, when compared with the composite biological host-implant electronics model populated with the previous data profiles as stored in device signature history 125, can result in an unacceptable prognosis of said active implant's performance going forward. Degraded emission profile 122 is then appended to device signature history 125.

Continue to refer to FIG. 10. Upon the decision to explant the active implant, implant explantation 114 is performed and explantation scan 107 is conducted at explantation hospital 99. Explantation scan 107 may be performed as a integral step of explantation 114, or directly afterwards. The explantation scan produces explantation emission profile 123 which is then compared with at least one of biological host-implant electronics and implant electronics models based on device signature history 125 to validate degraded emission profile 122 and active implant functional performance. Following explantation, the explanted active implant can be sent to for failure validation. Failure validation can comprise, among other modalities, failure validation scan 108. Failure validation scan 108 can be performed at analyzing hospital 100, implant manufacturing facility 95, or any appropriate location. Failure validation scan 108 can produce failure validation emission profile 124 that can be validated against implant electronics model populated with emission profiles from device signature history 125. Upon validation, the failure validation emission profile 124 can be appended to device signature history 125. Said active implant can then be disposed of, and device signature history 125 can be utilized to improve the implant electronics model incorporated into the present invention and future generations of said active implant.

The advantages of the present invention include, without limitation, diagnosis and monitoring of animal tracking devices heretofore not equipped with built in testing; detection, diagnosis, monitoring, and prognosis of multiple active implants in the same biological host; detection diagnosis, monitoring and prognosis of active implants to independently validate current built-in-test routines; ability to decrease unnecessary explantation and provide guidance to medical professionals, biologists and any life-sciences professional regarding the current and future state of active implants; monitoring with finer granularity the interactions between biological situations and active implants and implant electronics over time; etc. These and many other advantages will become obvious to those skilled in the art and should not be construed as describing all the advantages or limiting the advantages of the present invention; rather, the scope and spirit of the present invention's advantages should be construed as widely as is possible.

In a broader embodiment, the present invention is a diagnostic device that can wirelessly and non-invasively, using electromagnetic emissions from implanted electronics, detect and identify an active implant comprising electronics implanted in a biological host, diagnose the health of individual electronics as well as their health as an ensemble, and predict probable degradation of individual electronics, degradation of the electronic ensemble, and of the device itself in an automated fashion. This detection, identification, and diagnosis are based on the measurement of intentional and unintentional electromagnetic emissions that emanate from the implant electronics of the active implant in any given biological situation.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. An emissions measurement device for at least one electronic device implantable in a biological host comprising,
    at least one antenna,
    a receiver operable in a combination with said at least one antenna to collect unintentional electromagnetic emission(s) emitted by the at least one electronic device and is further operable to extract signature components from said unintentional electromagnetic emission(s), said unintentional emission(s) being separate or different from signals being intentionally emitted by the at least one electronic device,
processing algorithms comparing said signature components to one or both of a biological effect database and an electronic implant signature database,
a final scoring generating a score of said signature of the at least one electronic device, and
a data storage.

2. The emissions measurement device of claim 1, wherein the at least one electronic device is attached externally to the biological host.

3. The emissions measurement device of claim 1, wherein said at least one antenna is positioned on an external epidermal layer of the biological host.

4. The emissions measurement device of claim 3, wherein said at least one antenna is a conformal antenna adapted to conform to the external epidermal layer of the biological host.

5. The emissions measurement device of claim 4, wherein material properties of said conformal antenna match an impedance of a tissue of the biological host.

6. The emissions measurement device of claim 4, wherein material properties of said conformal antenna match an impedance of the external epidermal layer of the biological host.

7. The emissions measurement device of claim 1, wherein said receiver comprises a self-tuning matching network connected to said at least one antenna to match an impedance of a tissue of the biological host.

8. The emissions measurement device of claim 1, wherein said at least one antenna is a conformal antenna intended to conform to an external epidermal layer of the biological host.

9. The emissions measurement device of claim 1, wherein said at least one antenna is implanted in the biological host.

10. The emissions measurement device of claim 1, wherein said at least one antenna is positioned at a stand-off location from the biological host.

11. The emissions measurement device of claim 1, wherein the emissions measurement device detects the at least one electronic device implanted within the biological host.

12. The emissions measurement device of claim 1, wherein the emissions measurement device identifies the at least one electronic device implanted within the biological host.

13. The emissions measurement device of claim 1, wherein the emissions measurement device performs diagnostics on the at least one electronic device.

14. The emissions measurement device of claim 1, wherein the emissions measurement device performs diagnostics on the at least one electronic device, and
wherein the emissions measurement device receives a near field emission of the at least one electronic device to enhance an amplitude of said unintentional emission(s) collected at said receiver.

15. The measurement device of claim 1, wherein said at least one antenna is antenna structure located circumcentrically around the biological host that contains the at least one electronic device.

16. The measurement device of claim 15, wherein the biological host is moved through said antenna structure that surrounds the biological host.

17. The emissions measurement device of claim 15, wherein the biological host is located on a support structure that moves through said antenna structure for measurement purposes.

18. The emissions measurement device of claim 15, wherein said antenna structure is a loop antenna.

19. The emissions measurement device of claim 1, wherein said at least one antenna moves in relation to the biological host during measurement.

20. The emissions measurement device of claim 1, wherein said at least one antenna is mounted to a support structure that moves in relation to the biological host for measurement purposes.

21. The emissions measurement device of claim 1, which is configured to measure said unintentional emissions across at least one electromagnetic interface of a media with a relative permittivity greater than 1.

22. The emissions measurement device of claim 1, which is configured to measure said unintentional emissions of the at least one electronic device implanted in the biological host across at least one electromagnetic interface of a biological tissue.

23. The emissions measurement device of claim 1, wherein said emissions measurement device stores implanted electronic device histories.

24. The emissions measurement device of claim 1, further comprising a device for storing biological host information for modifying said signature.

25. The emissions measurement device of claim 1, operable, using said unintentional electromagnetic emission(s), to measure and diagnose a state of the at least one electronic device during manufacturing thereof.

26. The emissions measurement device of claim 1, operable, using said unintentional electromagnetic emission(s), to measure and diagnose a state of the at least one electronic device at an implantation facility.

27. The emissions measurement device of claim 1, operable, using said unintentional electromagnetic emission(s), to measure and diagnose a state of the at least one electronic device to verify integrity of the at least one electronic device prior to implantation.

28. The emissions measurement device of claim 1, wherein the at least one electronic device is an active implant and wherein the emissions measurement device is operable, using said unintentional electromagnetic emission(s), to measure and diagnose a state of the active implant immediately after implantation.

29. The emissions measurement device of claim 1, wherein the at least one electronic device is an active implant and wherein the emissions measurement device is operable, using said unintentional electromagnetic emission(s), to measure and diagnose a state of the active implant periodically throughout a lifetime of the active implant.

30. The emissions measurement device of claim 1, wherein the at least one electronic device is an active implant and wherein the emissions measurement device is operable, using said unintentional electromagnetic emission(s), to measure and diagnose a state of the active implant during degradation or failure of the active implant.

31. The emissions measurement device of claim 1, wherein the at least one electronic device is an active implant and wherein the emissions measurement device is operable, using said unintentional electromagnetic emission(s), to measure and diagnose a state of the active implant using the at least one of emission after explantation.

32. The emissions measurement device of claim 1, wherein the at least one electronic device is an active implant and wherein the emissions measurement device is operable, using said unintentional electromagnetic emission(s), to measure and diagnose a state of the active implant during post failure testing of the active implant.

33. The emissions measurement device of claim 1, further comprising a device capable of detecting the at least one electronic device whose location within the biological host changes over time.

34. The emissions measurement device of claim 1, wherein said emissions measurement device is capable of detecting the at least one electronic device that passes from inside to outside of the biological host.

35. The emissions measurement device of claim 1, wherein said emissions measurement device is capable of interpreting electromagnetic emissions whose signatures are modified by at least one biological tissue layer.

36. The emissions measurement device of claim 1, wherein the at least one electronic device is an implant and wherein said emissions measurement device is capable of determining at least one of a state of functionality and a state of degradation of the implant after the implant has been subjected to an electrical discharge.

37. The emissions measurement device of claim 1, wherein the at least one electronic device is an implant and wherein said emissions measurement device is capable of determining at least one of a state of functionality and a state of degradation of electronic components in the implant after the implant has been intentionally illuminated to power the electronic components thereof.

38. The emissions measurement device of claim 1, wherein the at least one electronic device is an implant and wherein said emissions measurement device is capable of determining at least one of a state of functionality and a state of degradation of electronic components in the implant after the electronic components have been illuminated.

39. The emissions measurement device of claim 1, wherein the at least one electronic device is an implant and wherein said emissions measurement device is capable of determining an identity of the implant by analyzing said unintentional electromagnetic emission(s).

40. The emissions measurement device of claim 1, wherein said emissions measurement device predicts a lifespan of any implanted electronics.

41. The emissions measurement device of claim 1, wherein the at least one electronic device is an implant and wherein said emissions measurement device predicts a lifespan of the implant.

42. The emissions measurement device of claim 1, wherein said emissions measurement device uses a measurement of said unintentional electromagnetic emission(s) to provide health monitoring of at the least one electronic device implanted in the biological host.

43. The emissions measurement device of claim 1, wherein said emissions measurement device uses a measurement of said unintentional electromagnetic emission(s) to provide diagnostics of the at least one electronic device implanted in the biological host.

44. The emissions measurement device of claim 1, wherein said emissions measurement device uses a measurement of said unintentional electromagnetic emission(s) to predict failure of the at least one electronic device implanted in the biological host.

45. The emissions measurement device of claim 1, wherein said emissions measurement device uses a measurement of said unintentional electromagnetic emissions to track at least one of a plurality of electronics aging effects on the at least one electronic device implanted in the biological host.

46. The emissions measurement device of claim 1, wherein said emissions measurement device uses a measurement of said unintentional electromagnetic emissions to provide a non-invasive detection of the at least one electronic device implanted in the biological host.

47. The emissions measurement device of claim 1, wherein said emissions measurement device uses a measurement of said unintentional electromagnetic emissions to provide a non-invasive identification of the at least one electronic device implanted in the biological host.

48. The emissions measurement device of claim 1, wherein said emissions measurement device uses a measurement of said unintentional electromagnetic emissions to non-invasively locate the at least one electronic device implanted in the biological host.

49. The emissions measurement device of claim 1, wherein said emissions measurement device uses a measurement of said unintentional electromagnetic emission to provide health monitoring of the at least one electronic device implanted in the biological host.

50. The emissions measurement device of claim 1, wherein said emissions measurement device verifies that the at least one electronic device implanted in a biological host has been implanted properly.

51. The emissions measurement device of claim 1, wherein said emissions measurement device is capable of detecting, identifying, and locating a non-stationary implant within the biological host.

52. The emissions measurement device of claim 1, wherein said emissions measurement device is capable of determining if a non-stationary implant has been ejected from the biological host.

53. The emissions measurement device of claim 1, wherein said emissions measurement device is capable of determining if the at least one electronic device is on or off at any given time.

54. The emissions measurement device of claim 1, wherein said emissions measurement device determines a degree of change observed as the at least one electronic device degrades.

55. The emissions measurement device of claim 1, wherein said emissions measurement device determines a degree of change observed as the at least one electronic device degrades, and ultimately fails, along with types of changes apparent in two different, but functionally connected devices.

56. The emissions measurement device of claim 1, wherein said emissions measurement device comprises a library of devices and device signatures to compare and assess a health of the at least one electronic device.

57. The emissions measurement device of claim 1, wherein said emissions measurement device comprises a substantially skull shaped fixture to compensate for at least one factor present in vivo for projection to a realistic environment when the at least one electronic device is implanted in the biological host.

58. The emissions measurement device of claim 1, wherein said emissions measurement device comprises a protocol for signature collection to assure proper collection of signature data without damaging the at least one electronic device implanted in the biological host.

59. The emissions measurement device of claim 1, wherein said emissions measurement device elucidates differences between different categories of failures.

60. The emissions measurement device of claim 1, wherein said emissions measurement device provides general electronic degradation characteristics that are general to any electronic implant.

61. The emissions measurement device of claim 1, wherein said emissions measurement device provides general electronic degradation characteristics that are specific to subsystems of classes of electronics implant in cases where the at least one electronic device implanted in the biological host is not fully identified.

62. The emissions measurement device of claim 1, further comprising said one or both of biological effect database and electronic implant signature database, wherein the at least one electronic device is an implant in the biological host and wherein said emissions measurement device uses said one or both of biological effect database and electronic implant signature database to provide for degradation detection of the implant.

63. The emissions measurement device of claim 1, wherein said emissions measurement device provides the ability to complete health monitoring on non-implanted electronics.

64. The emissions measurement device of claim 1, wherein the at least one electronic device is an implant and wherein said emissions measurement device uses changes in low power emissions from electronics embedded in the implant to determine health thereof.

65. The emissions measurement device of claim 1, wherein said unintentional emission(s) are enhanced by an electromagnetic field.

66. The emissions measurement device of claim 1, wherein an electromagnetic field is absorbed by the at least one electronic device and is subsequently re-emitted at a same or a different frequency as a frequency of the electromagnetic field and measured by the emission measurement device.

67. The emissions measurement device of claim 1, wherein an electromagnetic field is generated external to the biological host and projected onto the biological host.

68. The emissions measurement device of claim 1, wherein an electromagnetic field is generated internal to the biological host and internally launched into the biological host.

69. The emissions measurement device of claim 1, wherein said emissions measurement device comprises a biologically analogous fixture to control for some of factors present in vivo or in situ for projection to a realistic environment when said at least one electronic device is implanted in the biological host.

70. The emissions measurement device of claim 1, wherein said emissions measurement device is capable of observing multiple electronic devices in a single active implant simultaneously.

71. The emissions measurement device of claim 1, wherein said emissions measurement device is capable of diagnosing a state of a degradation of multiple electronic devices in a single active implant simultaneously.

72. The emissions measurement device of claim 1, wherein said emissions measurement device is capable of diagnosing a state of a degradation of multiple electronic devices in at least one of a plurality of active implants in a number of biological situations related to a single biological host.

73. The emissions measurement device of claim 1, wherein said emissions measurement device is capable of diagnosing a state of a degradation of multiple implant electronics in at least one of a plurality of active implants in a number of biological situations in a plurality of hosts simultaneously.

74. The emissions measurement device of claim 1, wherein said emissions measurement device is capable of predicting a future degradation of multiple electronics in a single active implant simultaneously.

75. The emissions measurement device of claim 1, wherein said emissions measurement device is capable of predicting a future degradation of multiple electronics in at least one of a plurality of active implants in a number of biological situations related to a single biological host.

76. The emissions measurement device of claim 1, wherein said emissions measurement device is capable of predicting a future degradation of multiple implant electronics in at least one of a plurality of active implants in a number of biological situations in a plurality of biological hosts simultaneously.

77. The emissions measurement device of claim 1, wherein said emissions measurement device is capable of assessing a risk of a failure of multiple electronics in a single active implant simultaneously.

78. The emissions measurement device of claim 1, wherein said emissions measurement device is capable of assessing a risk of a failure of multiple electronics in at least one of a plurality of active implants in a number of biological situations related to a single biological host.

79. The emissions measurement device of claim 1, wherein said emissions measurement device is capable of assessing a risk of a failure of multiple implant electronics in at least one of a plurality of active implants in a number of biological situations in a plurality of biological hosts simultaneously.

80. An emissions measurement device for at least one electronic device implanted in a biological host, comprising:
at least one antenna,
a receiver operable in a combination with said at least one antenna to collect unintentional electromagnetic emission(s) emitted by the at least one electronic device and is further operable to extract signature components from said unintentional electromagnetic emission(s), said unintentional emission(s) being separate or different from signals being intentionally emitted by the at least one electronic device,
processing algorithms comparing said signature components to one or both of a biological effect database and an electronic implant signature database,
a final scoring generating a score of said signature of the at least one electronic device, and
a data storage,
wherein said emissions measurement device is configured to measure said unintentional emission(s) across at least one electromagnetic interface of a biological tissue,
wherein said measurement device determines a degree of change observed as the at least one electronic device degrades,
wherein said emissions measurement device determines distinct electrical states for at least one component of the at least one electronic device, wherein the distinct electrical states are selected from the group comprising a nominal electronic function, a degraded electronic function, a failed electronic function and a combination thereof.

81. An emissions measurement device comprising,
at least one antenna,
a receiver operable in a combination with said at least one antenna to collect unintentional electromagnetic emission(s) emitted by the at least one electronic device and is further operable to extract signature components from said unintentional electromagnetic emission(s), said unintentional emission(s) being separate or different from signals being intentionally emitted by the at least one electronic device,
a data processing means comparing said signature components to one or both of a biological effect database and an electronic implant signature database and generating a score of said signature of the at least one electronic device, and
a data storage means,
wherein said emissions measurement device collects at least one unintended signatures emitted by the at least one electronic device embedded, as an implant, in a biological implant recipient.

82. The emissions measurement device of claim 81, wherein said emissions measurement device operates in a radio frequency (RF) range.

83. The emissions measurement device of claim 81, wherein said emissions measurement device operates in a microwave frequency range.

84. The emissions measurement device of claim 81, wherein said emissions measurement device operates at infrared wavelengths.

85. The emissions measurement device of claim 81, wherein said emissions measurement device operates at infrasonic wavelengths.

86. The emissions measurement device of claim 81, wherein said emissions measurement device operates at X-ray wavelengths.

87. The emissions measurement device of claim 81, wherein said emissions measurement device operates from DC to optical wavelengths.

88. A method to capture unintentional electromagnetic emissions from electronic device(s) implanted in a biological host, comprising:
  providing an emissions measurement device which comprises a data storage means, a receiver operable in a combination with at least one antenna to collect said unintentional electromagnetic emission(s) emitted by said electronic device(s) and is further operable to extract signature components from said unintentional electromagnetic emission(s), said unintentional emission(s) being separate or different from signals being intentionally emitted by said electronic device(s), and a processing means comparing said signature components to one or both of a biological effect database and an electronic implant signature database and generating a score of said signature of the at least one electronic device,
  collecting at least one unintentional electromagnetic emission from an implanted electronic device by means of said emission measurement device,
  encoding said at least one unintentional electromagnetic emission(s), and
  storing said at least one encoded unintentional electromagnetic emission(s) on said data storage means.

89. The method of claim 88, wherein the method further comprises creating a machine readable model from at least in part from the at least one encoded unintentional electromagnetic emission(s).

90. The method of claim 88, wherein a set of collected unintentional electromagnetic emissions data represents or characterizes distinct electrical states, wherein the distinct electrical states are selected from the group comprising a nominal electronic function, a degraded electronic function, a failed electronic function and a combination thereof.

91. The method of claim 88, further comprising:
  translating said at least one unintentional electromagnetic emission, wherein said unintentional electromagnetic emission(s) being collected in a free-space environment to mimic electromagnetic emissions that would pass through a biological tissue in vivo.

92. The method of claim 88, further comprising:
  providing a display,
  determining, with said processing means, a predictive risk assessment value derived from at least in part from said unintentional electromagnetic emission(s) received by said receiver, and
  displaying, on said display, a predictive risk assessment value to a user.

93. The method of claim 88, further comprising:
  providing a display,
  determining, with said processing means, a predictive risk assessment value derived from at least in part from said unintentional electromagnetic emission(s) received by said receiver,
  displaying, on said display, a predictive risk assessment value to a user, and
  wherein a set of collected electromagnetic emissions data represents or characterizes distinct electrical states, wherein the distinct electrical states are selected from the group comprising a nominal electronic function, a degraded electronic function, a failed electronic function and a combination thereof.

94. The method of claim 88, further comprising:
  validating an intended communication of said implanted electronic device(s).

95. The method of claim 88, further comprising:
  validating a radiation emission of said implanted electronic device(s).

96. The method of claim 88, further comprising:
  applying at least one algorithm to said encoded unintentional electromagnetic emission(s) for diagnosis of damage level and to predict failure of said implanted electronic device(s).

97. The method of claim 88, further comprising a statistical signature database that is developed by measuring a plurality of signatures from at least one physical device.

98. The method of claim 88, further comprising:
  developing electronic device signatures by inducing varying levels of deleterious damage to said electronic device(s).

99. The method of claim 88, further comprising:
  correlating collected electromagnetic emissions data to a diagnosable feature of device health.

100. The method of claim 88, further comprising:
  applying at least one algorithm, comprising an array of modules automatically selected to determine a health characteristic of said implanted electronic device(s), to said encoded unintentional electromagnetic emission(s).

101. The method of claim 88, further comprising:
  providing a centralized database,
  uploading, with said centralized database, a set of information to said data storage means,
  wherein said set of information is selected from the group comprising an updated biological effect, an updated electronic signature, a specific biological situation information, a specific biological situation, a specific active implant's history and a combination thereof.

102. The method of claim 88, further comprising:
  providing a centralized database,
  receiving, with said centralized database, a set of information from the data storage means,
  wherein said set of information is selected from the group comprising an updated biological effect, an updated electronic signature, a specific biological situation information, a specific biological situation, a specific active implant's history and a combination thereof.

103. The method of claim 88, further comprising:
  selecting a set of information from the group comprising an updated biological effect, an updated electronic signature, a specific biological situation information, a specific biological situation, a specific active implant's history, an at least one observed electronics degradation modes, newly observed biological effects and a combination thereof, storing said set of information in said data storage means,
retrieving said set of information in said data storage means,
removing personalized data from said set of information,
providing a centralized database, and
retrieving, with said centralized database, said set of retrieved information having said personalized data removed therefrom.

104. A method to generate a dataset of unintentional emissions from electronic device(s) implanted in a biological host, comprising:
providing a first emissions measurement device which comprises a first data storage means, a first receiver, and a first processing means,
providing a second emissions measurement device which comprises a second data storage means, a second receiver, and a second processing means,
collecting with said first emissions measurement device, at least one unintentional electromagnetic emission from an implanted electronic device, said at least one unintentional emission being separate or different from signals being intentionally emitted by said electronic device(s),
encoding said at least one unintentional electromagnetic emission, and
storing at least one encoded unintentional electromagnetic emission on said first data storage means.

105. The method of claim 104, further comprising:
selecting a set of information from the group comprising an updated biological effect, an updated electronic signature, a specific biological situation information, a specific biological situation, a specific active implant's history, an at least one observed electronics degradation modes, newly observed biological effects and a combination thereof,
storing said set of information in the first data storage means,
providing a centralized database,
retrieving, with said centralized database, a set of information from said first data storage means, and
uploading, with said centralized database uploads, said set of information to said second data storage means.

106. The method of claim 104, further comprising:
selecting a set of information from the group comprising an updated biological effect, an updated electronic signature, a specific biological situation information, a specific biological situation, a specific active implant's history, an at least one observed electronics degradation modes, newly observed biological effects and a combination thereof,
providing a centralized database, and
uploading, with said second data storage means, said set of information to said first data storage means.

107. The method of claim 104, further comprising:
sharing of at least one electromagnetic emission from said implanted electronic device between said first emissions measurement device and said second emission measurement device.

108. The method of claim 104, further comprising:
sharing of at least one electromagnetic emission from the implanted electronic devices between said first emissions measurement device and said second emission measurement device.

109. A system for analyzing unintentional electromagnetic emissions from an electrical device implanted in a biological host, comprising:
a receiver,
an antenna electrically coupled to said receiver, whereby said receiver collects said unintentional electromagnetic emissions emitted by the implanted electrical device and extracts signature components from said unintentional electromagnetic emissions, said unintentional emissions being separate or different from signals being intentionally emitted by the implanted electrical device,
a data processor comparing said signature components to one or both of a biological effect database and an electronic implant signature database and generating a score of said signature of the at least one electrical device,
a data storage,
a set of collected unintentional electromagnetic emissions data,
a model derived from said set of collected unintentional electromagnetic emissions data,
wherein said data processor determines at least one characteristic of the implanted electrical device through an application of said model to at least one signal received by said receiver related to an observed electromagnetic emission from the implanted electrical device.

110. The system of claim 109, wherein said set of collected electromagnetic emissions data represents or characterizes distinct electrical states.

111. The system of claim 109, wherein said set of collected electromagnetic emissions data represents or characterizes distinct electrical states, wherein said distinct electrical states are selected from the group comprising a nominal electronic function, a degraded electronic function, and a failed electronic function.

112. The system of claim 109, wherein said set of collected electromagnetic emissions data represents or characterizes distinct electrical states, wherein said distinct electrical states are selected from the group comprising a nominal electronic function, a degraded electronic function, a failed electronic function and a combination thereof.

113. The system of claim 109, wherein said set of collected electromagnetic emissions data represents or characterizes distinct electrical states for implantable electronics, wherein said distinct electrical states are selected from the group comprising a nominal electronic function, a degraded electronic function, a failed electronic function and a combination thereof.

114. The system of claim 109, wherein said set of collected electromagnetic emissions data represents or characterizes distinct electrical states for implanted electronics, wherein said distinct electrical states are selected from the group comprising a nominal electronic function, a degraded electronic function, a failed electronic function and a combination thereof.

115. The system of claim 109, wherein said set of collected electromagnetic emissions data represents or characterizes distinct electrical states for at least one component of said implanted electrical device, wherein said distinct electrical states are selected from the group comprising a nominal electronic function, a degraded electronic function, a failed electronic function and a combination thereof, and
wherein the data processor determines at least one characteristic of at least one component of said implanted electrical device through an application of said model to at least one signal received by the receiver related to an observed electromagnetic emission from said implanted electrical device.

116. The system of claim 109, wherein said model is in part derived from a knowledge of a biological situation related to said implanted electrical device.

117. The system of claim 109, wherein said processor determines a predictive risk assessment value at least in part from at least one signal received by said receiver.

118. The system of claim 109, further comprising:
a display,
wherein the processor determines a predictive risk assessment value at least in part from at least one signal received by said receiver, and
wherein said predictive risk assessment value is displayed by said display to a user.

119. The system of claim 109, wherein said antenna functions at least in part in the near field to collect electromagnetic emissions from said implanted electrical device through at least one biological tissue layer.

120. The system of claim 109, wherein said of collected electromagnetic emissions data comprises electromagnetic emissions data from implanted electrical devices and non-implanted electrical devices, and
wherein said model correlates parallel histories of electromagnetic emissions data from implanted electrical devices and non-implanted electrical devices.

121. The system of claim 109, wherein said set of collected electromagnetic emissions data comprises electromagnetic emissions data from implanted electrical devices and non-implanted electrical devices, and
wherein said model selects a relevant subset of data from said set of collected electromagnetic emissions data based on at least in part from a detected biological situation.

122. The system of claim 109, wherein said set of collected electromagnetic emissions data comprises electromagnetic emissions data from implanted electrical devices, and
wherein said model selects a relevant subset of data from said set of collected unintentional electromagnetic emissions data based on at least in part from a detected active implant.

123. The system of claim 109, wherein said model is used to measure or diagnose at least one characteristic of said implanted electrical device to verify that said implanted electrical device has not been tampered with.

124. A system for analyzing unintentional electromagnetic emissions from an implanted electrical device, comprising:
at least one receiver,
an array of at least two antennas electrically coupled to said at least one receiver, whereby said at least one receiver collects said unintentional electromagnetic emissions emitted by the implanted electrical device and extracts signature components from said unintentional electromagnetic emissions, said unintentional emissions being separate or different from signals being intentionally emitted by the implanted electrical device,
a data processor comparing said signature components to one or both of a biological effect database and an electronic implant signature database and generating a score of said signature of the at least one electrical device,
a data storage,
a set of collected electromagnetic emissions data,
a model derived from said set of collected electromagnetic emissions data,
wherein said data processor determines at least one characteristic of an implanted electrical device through an application of said model to at least one signal received by said at least one receiver of an observed electromagnetic emission from the implanted electrical device.

125. The system of claim 124, wherein said set of collected electromagnetic emissions data represents or characterizes distinct electrical states.

126. The system of claim 124, wherein said set of collected electromagnetic emissions data represents or characterizes distinct electrical states, wherein said distinct electrical states are selected from the group comprising a nominal electronic function, a degraded electronic function, a failed electronic function and a combination thereof.

127. The system of claim 124, wherein said at least one receiver comprises at least two receivers each connected to a separate antenna of said array of at least two antennas.

128. The system of claim 124, wherein said at least one receiver comprises at least two receivers each connected to separate antenna of said array of at least two antennas, and
wherein each of said at least two receivers is configured to conduct a different signal processing approach on the at least one signal received by each of said at least two receivers.

129. The system of claim 124, wherein said at least one receiver comprises at least two receivers each connected to a separate antenna of said array of at least two antennas, and
wherein said data processor uses at least one algorithm to provide a diagnostic state of the implanted electrical device.

130. The system of claim 124, wherein said array of at least two antennas functions at least in part in a near field to collect electromagnetic emissions from the implanted electrical device through at least one biological tissue layer.

* * * * *